(12) United States Patent
Hanson

(10) Patent No.: US 8,133,709 B2
(45) Date of Patent: Mar. 13, 2012

(54) TARGET SEQUENCES FOR SYNTHETIC MOLECULES

(75) Inventor: George Hanson, Madison, WI (US)

(73) Assignee: Life Technologies Corporation, Carlsbad, CA (US)

( * ) Notice: Subject to any disclaimer, the term of this patent is extended or adjusted under 35 U.S.C. 154(b) by 725 days.

(21) Appl. No.: 12/062,031

(22) Filed: Apr. 3, 2008

(65) Prior Publication Data

US 2009/0136983 A1  May 28, 2009

Related U.S. Application Data

(63) Continuation of application No. 10/970,635, filed on Oct. 22, 2004, now abandoned.

(60) Provisional application No. 60/513,031, filed on Oct. 22, 2003.

(51) Int. Cl.
*C12N 9/96* (2006.01)
*C07K 1/13* (2006.01)
*C07K 1/22* (2006.01)
*C07K 1/10* (2006.01)
*C07F 9/80* (2006.01)

(52) U.S. Cl. ........ 435/188; 530/412; 530/413; 530/402; 546/3

(58) Field of Classification Search .................. None
See application file for complete search history.

(56) References Cited

U.S. PATENT DOCUMENTS

| | | | |
|---|---|---|---|
| 5,932,474 | A | 8/1999 | Tsien et al. |
| 6,008,378 | A | 12/1999 | Tsien et al. |
| 6,054,271 | A | 4/2000 | Tsien et al. |
| 6,054,378 | A | 4/2000 | Skala et al. |
| 6,200,762 | B1 | 3/2001 | Zlokarnik et al. |
| 6,214,563 | B1 | 4/2001 | Negulescu et al. |
| 6,221,612 | B1 | 4/2001 | Knapp et al. |
| 6,451,569 | B1 | 9/2002 | Tsien et al. |
| 6,686,458 | B2 | 2/2004 | Tsien et al. |
| 6,858,590 | B2 | 2/2005 | Sallberg et al. |
| 7,138,503 | B2 | 11/2006 | Tsien et al. |
| 7,198,924 | B2 | 4/2007 | Chesnut et al. |
| 7,244,560 | B2 | 7/2007 | Chestnut et al. |
| 7,524,972 | B2 | 4/2009 | Tsien et al. |
| 2002/0136740 | A1 | 9/2002 | Sallberg et al. |
| 2005/0095615 | A1 | 5/2005 | Welch et al. |
| 2005/0136449 | A1 | 6/2005 | Hanson |
| 2005/0239135 | A1 | 10/2005 | Bogoev |
| 2006/0051852 | A1 | 3/2006 | Smith et al. |
| 2006/0110788 | A1 | 5/2006 | Kudlicki et al. |
| 2009/0136983 | A1 * | 5/2009 | Hanson ........................... 435/29 |
| 2009/0176975 | A1 | 7/2009 | Yim et al. |

FOREIGN PATENT DOCUMENTS

WO  WO-02/046372  6/2002
WO  WO-2005/054427  6/2005

OTHER PUBLICATIONS

Adams et al., "New Biarsenical Ligands and Tetracysteine Motifs for Protein Labeling in Vitro and in Vivo: Synthesis and Biological Applications", *Journal of the American Chemical Society*, vol. 124, Issue 21, May 2, 2002, 6063-6076.
Gaietta et al., "Multicolor and Electron Microscopic Imaging of Connexin Trafficking", *Science*, vol. 296, Issue 5567, Apr. 19, 2002, 503-507.
Griffin et al., "Fluorescent labeling of Recombinant Proteins in Living Cells with Flash", *Methods in Enzymology*, vol. 327, 2000, 565-578.
Griffin et al., "Specific Covalent Labeling of Recombinant Protein Molecules Inside Live Cells", *Science*, vol. 281, Issue 5374, Jul. 10, 1998, 269-272.
Hayashi et al., "Complete Genome Sequence of Enterohemorrhagic *Eschelichia coli* O157:H7 and Genomic Comparison with a Laboratory Strain K-12", *DNA Research*, vol. 8, No. 1, Feb. 2001, 11-22.
Ho et al., "Dimeric ligands define a role for transcriptional activation domains in reinitiation", *Nature*, vol. 382, Issue 6594, Aug. 29, 1996, 822-826.
International Application No. PCT/US2004/035142, International Search Report mailed on Aug. 31, 2006.
Invitrogen Corporation, Catalog No. K9600-01, 2003.
Perna et al., "Genome sequence of enterohaemorrhagic *Escherichia coli* O157:H7", *Nature*, vol. 409, No. 6819, Jan. 25, 2001, 529-533.
Roof et al., "slyD, a Host Gene required for X174 Lysis, Is Related to the FK506-binding Protein Family of Peptideyl-Prolyl Cis-Trans-Isomerases", *Journal of Biological Chemistry*, vol. 269, No. 4, Jan. 28, 1994, 2902-2910.
Spencer, "Controlling signal transduction with synthetic ligands", *Science*, vol. 262, No. 5136, Nov. 12, 1993, 1019-1024.
Stroffekova, "The protein-labeling reagent Flash-EDT2 binds not only to CCXXCC motifs but also non-specifically to endogenous cysteine-rich proteins", *European Journal of Physiology*, vol. 442, Issue 6, Sep. 2001, 859-866.
U.S. Appl. No. 10/970,635, Non-Final Office Action mailed on Aug. 9, 2006.
U.S. Appl. No. 10/970,635, Non-Final Office Action mailed on Oct. 5, 2007.
U.S. Appl. No. 10/970,635, Response to Non-Final Office Action filed Dec. 11, 2006.
Wei et al., "Complete Genome Sequence and Comparative Genomics of *Shigella flexneri* seotype 2a strain 2457T", *Infection and Immunity*, vol. 71, No. 5, May 2003, 2775-2786.
Wei et al., "Complete Genome Sequence and Comparative Genomics of *Shigella flexneri* Serotype 2a Strain 2457T", Erratum, *Infection and Immunity*, vol. 71, No. 7, Jul. 2003, 4223.
Welch, "Extensive mosaic structure revealed by the complete genome sequence of uropathogenic *Escherichia coli*", *Proceedings of the National Academy of Sciences (PNAS)*, vol. 99, No. 26, Dec. 24, 2002, 17020-107024.
Wulfing, "An *Escherichia coli* Protein Consisting of a Domain Homologous to FK506-Binding Proteins (FKBP) and a New Metal Binding Motif", *The Journal of Biological Chemistry*, vol. 269, Issue 4, Jan. 28, 1994, 2895-2901.

\* cited by examiner

*Primary Examiner* — Michael Burkhart

(57) ABSTRACT

The invention is based on the discovery that certain biarsenical molecules react with specified target sequences, thereby providing a facile means for labeling polypeptides containing the target sequence. The invention is useful in creating stable mammalian cell lines expressing a certain tetracysteine tagged polypeptides, thereby overcoming toxicity associated with native tetracysteine. In addition, the invention allows for orthogonal labeling of polypeptides, thereby allowing for the observation of protein-protein interactions and conformational changes in proteins, for example.

23 Claims, 17 Drawing Sheets

TAUTOMERS (III)

(IV)

SALTS (IV)

(V)

ANHYDRIDES (VI)

(VII)

BIOTIN CONJUGATE

ENZYME CONJUGATE VIA ε-AMINO
GROUP OF A LYSINE

PHOSPHORESCENCE (IN ABSENCE OF $O_2$)
SINGLET OXYGEN GENERATION WITH $O_2$

Ln=Tb, Eu: LUMINESCENCE

METAL CHELATION

SPIN LABEL (ELECTRON PARAMAGNETIC RESONANCE)

PHOTOSENSITIZER OF HYDROXYL
RADICAL FORMATION $R^3=R^4=^3H$ OR $^{125}I$: RADIOACTIVITY
$R^3=R^4+I$ OR TIOH: HEAVY ATOMS
FOR X-RAY SCATTERING

PARAMAGNETIC ION INCREASING
PROTON RELAXIVITY $^{19}F$ NMR PROBE

FLUORESCENT COMPLEX

FLUORESCENT COMPLEX

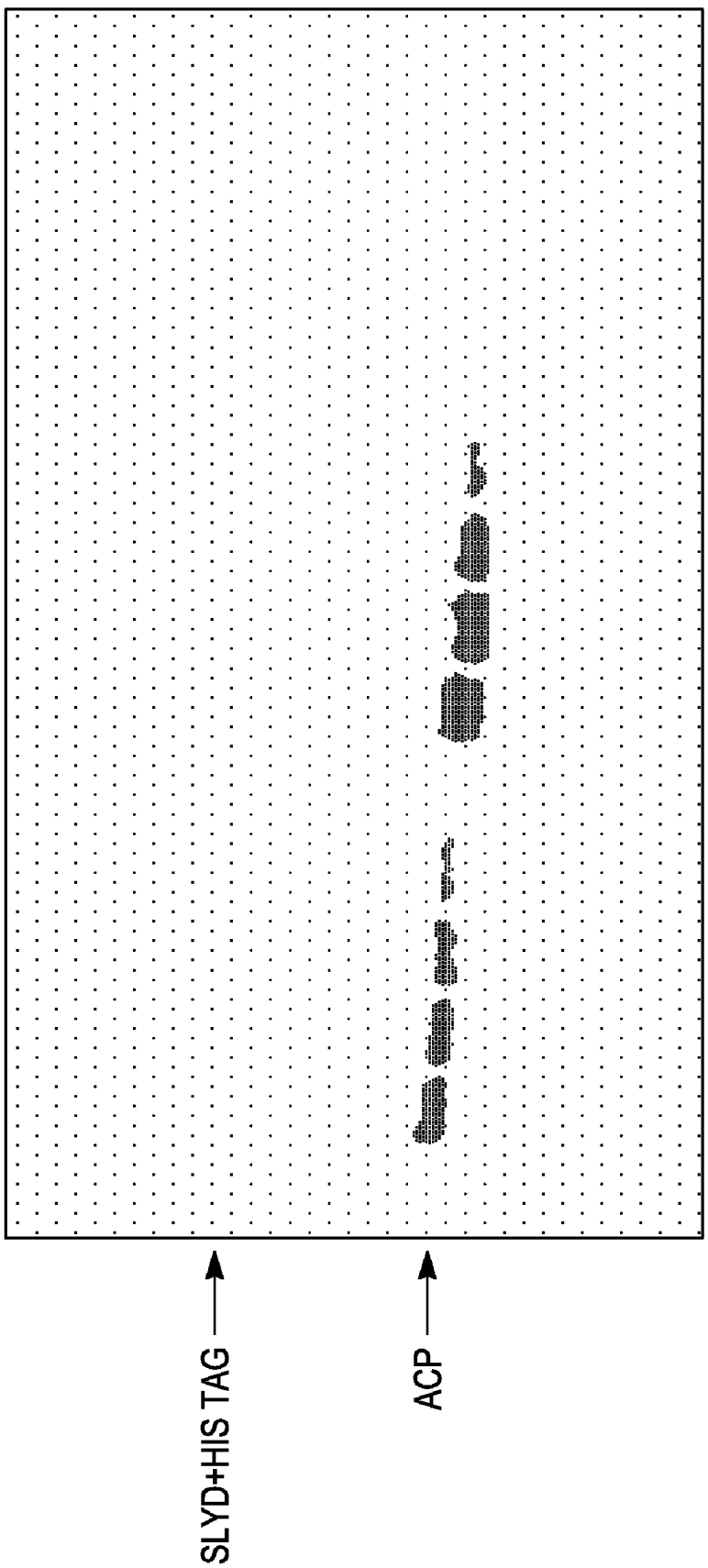

TARGET SEQUENCES FOR SYNTHETIC MOLECULES

CROSS REFERENCE TO RELATED APPLICATIONS

This application is a continuation of, and claims priority under 35 USC §120 to, U.S. patent application Ser. No. 10/970,635 filed Oct. 22, 2004, now abandoned which claims the benefit of U.S. Provisional Patent Application No. 60/513,031 filed Oct. 22, 2003, the disclosure of which is incorporated by reference herein in its entirety.

BACKGROUND OF THE INVENTION

1. Field of the Invention

This invention relates generally to compositions and methods for labeling molecules, and more specifically to small, synthetic molecules that react with target sequences.

2. Background Information

Many techniques in the biological sciences require attachment of labels to molecules, such as polypeptides. For example, the location of a polypeptide within a cell can be determined by attaching a fluorescent label to the polypeptide.

Traditionally, labeling has been accomplished by chemical modification of purified polypeptides. For example, the normal procedures for fluorescent labeling require that the polypeptide be covalently reacted in vitro with a fluorescent dye, then repurified to remove excess dye and/or any damaged polypeptide. Using this approach, problems of labeling stoichiometry and disruption of biological activity are frequently encountered. Furthermore, to study a chemically modified polypeptide within a cell, microinjection can be required. These processes can be tedious and typically cannot be performed on a large population of cells.

Thiol- and amine-reactive chemical labels exist and can be used to label polypeptides within a living cell. However, these chemical labels are promiscuous. Such labels cannot react with a particular cysteine or lysine of a particular polypeptide within a living cell that has numerous other reactive thiol and amine groups.

Another method of intracellular labeling of polypeptides in living cells has involved genetically engineering fusion polypeptides that include green fluorescent protein (GFP) and a polypeptide of interest. However, GFP is limited in versatility because it cannot reversibly label the polypeptide. In addition, GFP is a full size protein of 238 amino acids. GFP's large size frequently perturbs the protein interest upon binding. In addition, the spectroscopic read-out for GFP is at an emission maxima of up to 529 nm. Although red emitting fluorescent proteins are known to the art, their development has been slow and their utility has been greatly restricted.

Recently, another method of intracellular labeling of polypeptides in living cells wherein a fluorescent biarsenical compound binds to a tetracysteine motif having the sequence Cys-Cys-Xaa-Xaa-Cys-Cys (SEQ. ID NO: 1) (wherein Xaa is any amino acid other than cysteine). C. Griffin, et al., science 1998, 281, 269-272; U.S. Pat. Nos. 6,451,569 B1, 6,008,378, 6,054,271, and 5,932,474, all of which are herein incorporated by reference. The Cys-Cys-Xaa-Xaa-Cys-Cys (SEQ ID NO: 1) motif occurs infrequently in nature such that recombinant addition of this motif to a target protein provides a selective method of functionally tagging a defined protein. However, additional motifs which occur infrequently in nature and are capable of binding biarsenical molecules would be useful.

SUMMARY OF THE INVENTION

The invention is based, in part, on the discovery that certain biarsenical molecules react with specified cysteine target sequences, preferably a tetracysteine target sequence, thereby providing a means for labeling polypeptides containing the cysteine target sequence. In particular, the invention is useful in producing stable mammalian cell lines expressing a cysteine tagged polypeptide, thereby overcoming toxicity associated with native tetracysteine. In addition, the invention provides orthogonal labeling of polypeptides, thereby allowing for the observation of protein-protein interactions and conformational changes in proteins, for example.

In one embodiment, there are provided vectors including a nucleic acid sequence encoding a bonding partner, wherein the nucleic acid sequence encoding the bonding partner includes a nucleic acid sequence encoding a carrier polypeptide and a nucleic acid sequence encoding a target sequence, wherein the nucleic acid sequence encoding the target sequence is heterologous to the nucleic acid sequence encoding the carrier polypeptide, and the target sequence comprises at least 2 cysteines and has the sequence of Cys-Cys-$R_n$, whether R is any amino acid, including both D & L forms, and n is an integer from 1-100, and wherein when $n \geq 2$, each R is selected independently from every other R in the sequence, but wherein the target sequence cannot be Cys-Cys-Xaa-Xaa-Cys-Cys (SEQ. ID NO: 1) wherein Xaa can be any amino acid, and wherein the target sequence reacts with a biarsenical molecule having the formula:

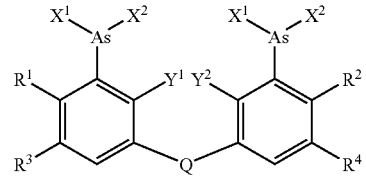

and tautomers, anhydrides, and salts thereof;

wherein:

each $X^1$ or $X^2$ is independently Cl, Br, I, $OR^a$, or $SR^a$, or $X^1$ and $X^2$ together with the arsenic atom form a ring having the formula:

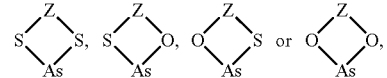

$R^a$ is H, $C_1$-$C_4$ alkyl, $CH_2CH_2OH$, $CH_2COOH$, or CN;

Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;

$Y^1$ and $Y^2$, are each independently H or $CH_3$, or $Y^1$ and $Y^2$ together form a ring such that the biarsenical molecule has the formula

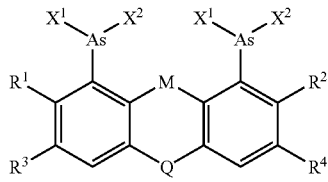

wherein:

M is O, S, $CH_2$, $C(CH_3)_2$, or NH;

$R^1$ and $R^2$ are each independently $OR^a$, OAc, $NR^aR^b$, or H;

$R^3$ and $R^4$ are each independently H, F, Cl, Br, I, $OR^a$, or $R^a$; or $R^1$ together with $R^3$, or $R^2$ together with $R^4$, or both, form a ring in which (i) one of $R^1$ or $R^3$ is $C_2$-$C_3$ alkyl and the other is $NR^a$ and (ii) one of $R^2$ and $R^4$ is $C_2$-$C_3$ alkyl and the other is $NR^a$;

$R^b$ is H, $C_1$-$C_4$ alkyl, $CH_2CH_2OH$, $CH_2COOH$, or CN;

Q is $CR^aR^b$, $CR^aOR^b$, C=O, or a spirolactone having the formula:

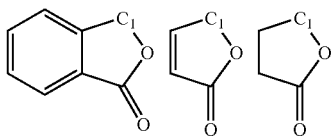

wherein the spiro linkage is formed at $C_1$.

In another embodiment, there are provided methods of labeling a carrier molecule. Such methods can be performed, for example, by a) providing a bonding partner including the carrier molecule and a target sequence, and b) contacting the bonding partner with a biarsenical molecule under conditions wherein the biarsenical molecule reacts with the target sequence, wherein the target sequence comprises at least 2 cysteines and has the sequence of Cys-Cys-$R_n$, whether R is any amino acid and n is an integer from 1-100, and wherein when n≧2, each R is selected independently from every other R in the sequence, but wherein the target sequence cannot be Cys-Cys-Xaa-Xaa-Cys-Cys (SEQ. ID NO: 1) wherein Xaa can be any amino acid, and, wherein the biarsenical molecule has the formula:

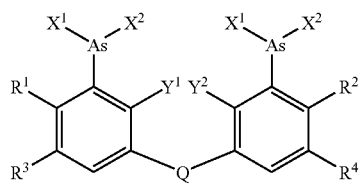

and tautomers, anhydrides, and salts thereof;

wherein:

each $X^1$ or $X^2$ is independently Cl, Br, I, $OR^a$, or $SR^a$, or $X^1$ and $X^2$ together with the arsenic atom form a ring having the formula:

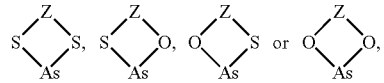

$R^a$ is H, $C_1$-$C_4$ alkyl, $CH_2CH_2OH$, $CH_2COOH$, or CN;

Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;

$Y^1$ and $Y^2$ are each independently H or $CH_3$, or $Y^1$ and $Y^2$ together form a ring such that the biarsenical molecule has the formula

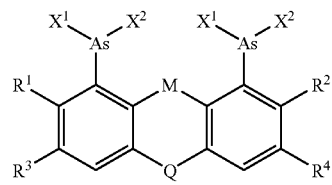

wherein:

M is O, S, $CH_2$, $C(CH_3)_2$, or NH;

$R^1$ and $R^2$ are each independently $OR^a$, OAc, $NR^aR^b$, or H;

$R^3$ and $R^4$ are each independently H, F, Cl, Br, I, $OR^a$, or $R^a$; or $R^1$ together with $R^3$, or $R^2$ together with $R^4$, or both, form a ring in which (i) one of $R^1$ or $R^3$ is $C_2$-$C_3$ alkyl and the other is $NR^a$ and (ii) one of $R^2$ and $R^4$ is $C_2$-$C_3$ alkyl and the other is $NR^a$;

$R^b$ is H, $C_1$-$C_4$ alkyl, $CH_2CH_2OH$, $CH_2COOH$, or CN;

Q is $CR^aR^b$, $CR^aOR^b$, C=O, or a spirolactone having the formula:

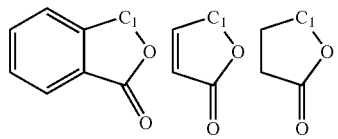

wherein the spiro linkage is formed at $C_1$.

In another embodiment, there are provided kits including a biarsenical molecule having the structure:

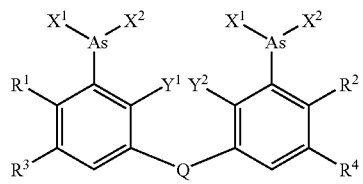

and tautomers, anhydrides, and salts thereof;

wherein:
each $X^1$ or $X^2$ is independently Cl, Br, I, $OR^a$, or $SR^a$, or $X^1$ and $X^2$ together with the arsenic atom form a ring having the formula:

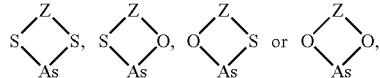

$R^a$ is H, $C_1$-$C_4$ alkyl, $CH_2CH_2OH$, $CH_2COOH$, or CN;
Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;
$Y^1$ and $Y^2$ are each independently H or $CH_3$, or
$Y^1$ and $Y^2$ together form a ring such that the biarsenical molecule has the formula

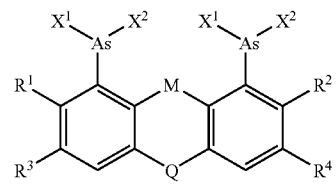

wherein:
M is O, S, $CH_2$, $C(CH_3)_2$, or NH;
$R^1$ and $R^2$ are each independently $OR^a$, OAc, $NR^aR^b$, or H;
$R^3$ and $R^4$ are each independently H, F, Cl, Br, I, $OR^a$, or $R^a$; or
$R^1$ together with $R^3$, or $R^2$ together with $R^4$, or both, form a ring in which
(i) one of $R^1$ or $R^3$ is $C_2$-$C_3$ alkyl and the other is $NR^a$ and
(ii) one of $R^2$ and $R^4$ is $C_2$-$C_3$ alkyl and the other is $NR^a$;
$R^b$ is H, $C_1$-$C_4$ alkyl, $CH_2CH_2OH$, $CH_2COOH$, or CN;
Q is $CR^aR^b$, $CR^aOR^b$, C=O, or a spirolactone having the formula:

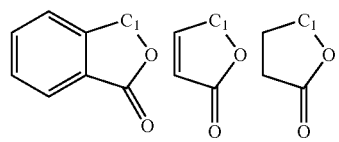

wherein the spiro linkage is formed at $C_1$; and a bonding partner including a target sequence, wherein the target sequence comprises at least 2 cysteines and has the sequence of Cys-Cys-$R_n$, whether R is any amino acid and n is an integer from 1-100, and wherein when n≥2, each R is selected independently from every other R in the sequence, but wherein the target sequence cannot be Cys-Cys-Xaa-Xaa-Cys-Cys (SEQ. ID NO: 1), wherein Xaa can be any amino acid and wherein the target sequence reacts with the biarsenical molecule.

In yet another embodiment, there are provided complexes including a biarsenical molecule and a target sequence, wherein the target sequence is a tetracysteine sequence comprising the residues Cys-Cys-X-X-X-X-X-X-X-Cys-X-Cys-X (SEQ. ID NO: 2), wherein X is any amino acid, and wherein the target sequence reacts with the biarsenical molecule, wherein the biarsenical molecule has the structure:

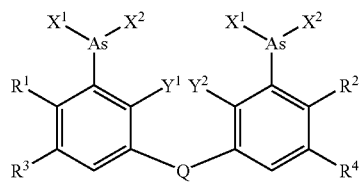

and tautomers, anhydrides, and salts thereof;
wherein:
each $X^1$ or $X^2$ is independently Cl, Br, I, $OR^a$, or $SR^a$, or $X^1$ and $X^2$ together with the arsenic atom form a ring having the formula:

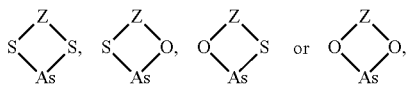

$R^a$ is H, $C_1$-$C_4$ alkyl, $CH_2CH_2OH$, $CH_2COOH$, or CN;
Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;
$Y^1$ and $Y^2$ are each independently H or $CH_3$, or
$Y^1$ and $Y^2$ together form a ring such that the biarsenical molecule has the formula

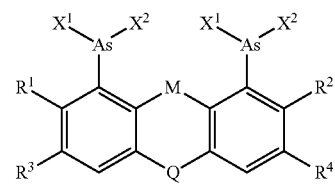

wherein:
M is O, S, $CH_2$, $C(CH_3)_2$, or NH;
$R^1$ and $R^2$ are each independently $OR^a$, OAc, $NR^aR^b$, or H;
$R^3$ and $R^4$ are each independently H, F, Cl, Br, I, $OR^a$, or $R^a$; or
$R^1$ together with $R^3$, or $R^2$ together with $R^4$, or both, form a ring in which
(i) one of $R^1$ or $R^3$ is $C_2$-$C_3$ alkyl and the other is $NR^a$ and
(ii) one of $R^2$ and $R^4$ is $C_2$-$C_3$ alkyl and the other is $NR^a$;
$R^b$ is H, $C_1$-$C_4$ alkyl, $CH_2CH_2OH$, $CH_2COOH$, or CN;
Q is $CR^aR^b$, $CR^aOR^b$, C=O, or a spirolactone having the formula:

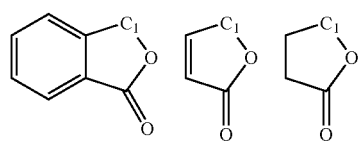

wherein the spiro linkage is formed at $C_1$.
In still another embodiment, there are provided methods for purifying bonding partners. Such methods can be performed for example, by a) providing a bonding partner comprising a target sequence, wherein the target sequence comprises at least 2 cysteines and has the sequence of Cys-Cys-$R_n$, whether R is any amino acid and n is an integer from 1-100, and wherein when $n \geq 2$, each R is selected independently from every other R in the sequence, but wherein the target sequence cannot be Cys-Cys-Xaa-Xaa-Cys-Cys (SEQ. ID NO: 1) wherein Xaa can be any amino acid, and wherein the target sequence reacts with a biarsenical molecule having the structure:

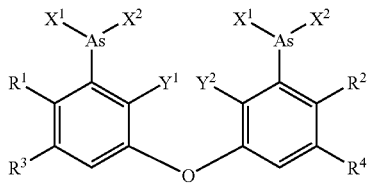

and tautomers, anhydrides, and salts thereof;
  wherein:
    each $X^1$ or $X^2$ is independently Cl, Br, I, $OR^a$, or $SR^a$, or
    $X^1$ and $X^2$ together with the arsenic atom form a ring having the formula:

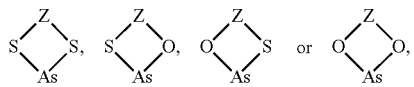

$R^a$ is H, $C_1$-$C_4$ alkyl, $CH_2CH_2OH$, $CH_2COOH$, or CN;
    Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;
    $Y^1$ and $Y^2$ are each independently H or $CH_3$, or
    $Y^1$ and $Y^2$ together form a ring such that the biarsenical molecule has the formula

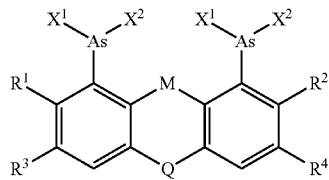

wherein:
    M is O, S, $CH_2$, $C(CH_3)_2$, or NH;
    $R^1$ and $R^2$ are each independently $OR^a$, OAc, $NR^aR^b$, or H;
    $R^3$ and $R^4$ are each independently H, F, Cl, Br, I, $OR^a$, or $R^a$; or
    $R^1$ together with $R^3$, or $R^2$ together with $R^4$, or both, form a ring in which
      (i) one of $R^1$ or $R^3$ is $C_2$-$C_3$ alkyl and the other is $NR^a$ and
      (ii) one of $R^2$ and $R^1$ is $C_2$-$C_3$ alkyl and the other is $NR^a$;
    $R^b$ is H, $C_1$-$C_4$ alkyl, $CH_2CH_2OH$, $CH_2COOH$, or CN;
    Q is $CR^aR^b$, $CR^aOR^b$, C=O, or a spirolactone having the formula:

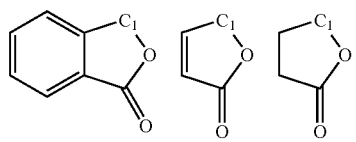

wherein the spiro linkage is formed at $C_1$;
  b) contacting the bonding partner with the biarsenical molecule, wherein the biarsenical molecule is coupled to a solid phase, and
  c) eluting the bonding partner from the biarsenical molecule by contacting the biarsenical molecule with a dithiol.

In another embodiment, there are provided methods for cross-linking two bonding partners. Such methods can be performed for example, by
  a) providing a tetraarsenical molecule capable of reacting with a first and a second target sequence; and
  b) contacting the tetraarsenical molecule with at least two bonding partners under conditions effective for the tetraarsenical molecule to react with the first and the second target sequences, the first bonding partner comprising the first target sequence, the second bonding partner comprising the second target sequence,
wherein at least one of the target sequences comprises at least 2 cysteines and has the sequence of Cys-Cys-$R_n$, whether R is any amino acid and n is an integer from 1-100, and wherein when $n \geq 2$, each R is selected independently from every other R in the sequence, but wherein the target sequence cannot be Cys-Cys-Xaa-Xaa-Cys-Cys (SEQ. ID NO: 1) wherein Xaa can be any amino acid, and wherein the target sequence reacts with a biarsenical molecule having the structure:

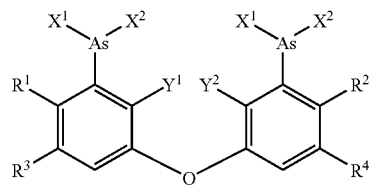

and tautomers, anhydrides, and salts thereof;
  wherein:
    each $X^1$ or $X^2$ is independently Cl, Br, I, $OR^a$, or $SR^a$, or
    $X^1$ and $X^2$ together with the arsenic atom form a ring having the formula:

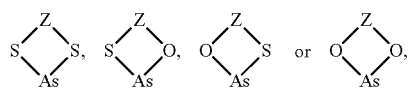

$R^1$ is H, $C_1$-$C_4$ alkyl, $CH_2CH_2OH$, $CH_2COOH$, or CN;
    Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;

$Y^1$ and $Y^2$ are each independently H or $CH_3$, or
$Y^1$ and $Y^2$ together form a ring such that the biarsenical molecule has the formula

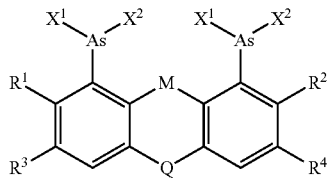

wherein:
  M is O, S, $CH_2$, $C(CH_3)_2$, or NH;
  $R^1$ and $R^2$ are each independently $OR^a$, OAc, $NR^aR^b$, or H;
  $R^3$ and $R^4$ are each independently H, F, Cl, Br, I, $OR^a$, or $R^a$; or
  $R^1$ together with $R^3$, or $R^2$ together with $R^4$, or both, form a ring in which
  (i) one of $R^1$ or $R^3$ is $C_2$-$C_3$ alkyl and the other is $NR^a$ and
  (ii) one of $R^2$ and $R^4$ is $C_2$-$C_3$ alkyl and the other is $NR^a$;
  $R^b$ is H, $C_1$-$C_4$ alkyl, $CH_2CH_2OH$, $CH_2COOH$, or CN;
  Q is $CR^aR^b$, $CR^aOR^b$, C=O, or a spirolactone having the formula:

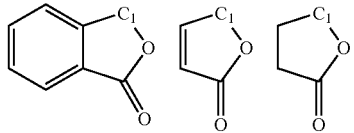

wherein the spiro linkage is formed at $C_1$.

In a still further embodiment, there are provided isolated polypeptides including a sequence Cys-Cys-$X_1$-$X_1$-$X_2$-$X_1$-$X_3$-$X_1$-$X_1$-Cys-$X_1$-Cys-$X_2$ (SEQ ID NO: 3), wherein:
  $X_1$ is an amino acid having a non-polar side chain,
  $X_2$ is an amino acid having a basic side chain, and
  $X_3$ is an amino acid having a non-ionic polar side chain.

Sequence ID Numbers

```
SEQ. ID NO: 4 (SlyD Native)
MKVAKDLVVSLAYQVRTEDGVLVDESPVSAPLDYLHGHGSLISGLET

ALEGHEVGDKFDVAVGANDAYGQYDENLVQRVPKDVFMGVDELQV

GMRFLAETDQGPVPVEITAVEDDHVVVDGNHMLAGQNLKFNVEVVA

IREATEEELAHGHVHGAHDHHHDHDHDGCCGGHGHDHGHEHGGEG

CCGGKGNGGCGCH

SEQ. ID NO: 5 (SlyD tetracysteine sequence)
CCGGKGNGGCGC

SEQ. ID NO: 6 (AcpS)
MAILGLGTDIVEIARIEAVIARSGDRLARRVLSDNEWAIWKTHHQPVR

FLAKRFAVKEAAAKAFGTGIRNGLAFNQFEVFNDELGKPRLRLWGEA

LKLAEKLGVANMHVTLADERHYACATVIIESGGEGCCGGKGNGGCG

CH

SEQ. ID NO: 7 (ACP)
MSTIEERVKKIIGEQLGVKQEEVTNNASFVEDLGADSLDTVELVMALE

EEFDTEIPDEEAEKITTVQAAIDYINGHQACCPGCC

SEQ. ID NO: 8 (SlyD + His tag)
MRGSHHHHHHGMASMTGGQQMGRDLYDDDDKDPMKVAKDLVVSL

AYQVRTEDGVLVDESPVSAPLDYLHGHGSLISGLETALEGHEVGDKFD

VAVGANDAYGQYDENLVQRVPKDVFMGVDELQVGMRFLAETDQGP

VPVEITAVEDDHVVVDGNHMLAGQNLKFNVEVVAIREATEEELAHGH

VHGAHDHHHDHDHDGCCGGHGHDHGHEHGGEGCCGGKGNGGCGC

H

SEQ. ID NO: 9 (SlyD C167A/C168A)
MRGSHHHHHHGMASMTGGQQMGRDLYDDDDKDPMKVAKDLVVSL

AYQVRTEDGVLVDESPVSAPLDYLHGHGSLISGLETALEGHEVGDKFD

VAVGANDAYGQYDENLVQRVPKDVFMGVDELQVGMRFLAETDQGP

VPVEITAVEDDHVVVDGNHMLAGQNLKFNVEVVAIREATEEELAHGH

VHGAHDHHHDHDHDGAAGGHGHDHGHEHGGEGCCGGKGNGGCGC

H

SEQ. ID NO: 10 (SlyD trunc171)
MRGSHHHHHHGMASMTGGQQMGRDLYDDDDKDPMKVAKDLVVSL

AYQVRTEDGVLVDESPVSAPLDYLHGHGSLISGLETALEGHEVGDKFD

VAVGANDAYGQYDENLVQRVPKDVFMGVDELQVGMRFLAETDQGP

VPVEITAVEDDHVVVDGNHMLAGQNLKFNVEVVAIREATEEELAHGH

VHGAHDHHHDHDHDGCCGGH

SEQ. ID NO: 11 (Calmodulin)
MADQLTCCEQCCFKEAFSLFDKDGDGTITTKELGTVMRSLGQNPTEA

ELQDMINEVDADGNGTIYFPEFLTMMARKMKDTDSEEEIREAFRVFD

KDGNGYISAAELRHVMTNLGEKLTDEEVDEMIREADIDGDGQVNYEE

FVQMMTAK

SEQ. ID NO: 12
AGCCTGCTTT TTTATACTAA CTTGAGC

SEQ. ID NO: 13
GTTCAGCTTT TTTATACTAA GTTGGCA

SEQ. ID NO: 14
AGCCTGCTTT TTTATACTAA GTTGGCA

SEQ. ID NO: 15
GTTCAGCTTT TTTATACTAA CTTGAGC

SEQ. ID NO: 16
AGCCTGCTTT TTTGTACAAA CTTGT

SEQ. ID NO: 17
GTTCAGCTTT TTTGTACAAA GTTGGCA

SEQ. ID NO: 18
AGCCTGCTTT TTTGTACAAA GTTGGCA

SEQ. ID NO: 19
GTTCAGCTTT TTTGTACAAA CTTGT

SEQ. ID NO: 20
ACCCAGCTTT CTTGTACAAA GTGGT

SEQ. ID NO: 21
GTTCAGCTTT CTTGTACAAA GTTGGCA
```

SEQ. ID NO: 22
ACCCAGCTTT CTTGTACAAA GTTGGCA

SEQ. ID NO: 23
GTTCAGCTTT CTTGTACAAA GTGGT

SEQ. ID NO: 24
CAACTTTATT ATACAAAGTT GT

SEQ. ID NO: 25
GTTCAACTTT ATTATACAAA GTTGGCA

SEQ. ID NO: 26
CAACTTTATT ATACAAAGTT GGCA

SEQ. ID NO: 27
GTTCAACTTT ATTATACAAA GTTGT

SEQ. ID NO: 28
CAACTTTTCT ATACAAAGTT GT

SEQ. ID NO: 29
GTTCAACTTT TCTATACAAA GTTGGCA

SEQ. ID NO: 30
CAACTTTTCT ATACAAAGTT GGCA

SEQ. ID NO: 31
GTTCAACTTT TCTATACAAA GTTGT

SEQ. ID NO: 32
CAACTTTTGT ATACAAAGTT GT

SEQ. ID NO: 33
GTTCAACTTT TGTATACAAA GTTGGCA

SEQ. ID NO: 34
CAACTTTTGT ATACAAAGTT GGCA

SEQ. ID NO: 35
GTTCAACTTT TGTATACAAA GTTGT

SEQ. ID NO: 36
CAACTTTTTC GTACAAAGTT GT

SEQ. ID NO: 37
GTTCAACTTT TTCGTACAAA GTTGGCA

SEQ. ID NO: 38
CAACTTTTTC GTACAAAGTT GGCA

SEQ. ID NO: 39
GTTCAACTTT TTCGTACAAA GTTGT

SEQ. ID NO: 40
CAACTTTTTG GTACAAAGTT GT

SEQ. ID NO: 41
GTTCAACTTT TTGGTACAAA GTTGGCA

SEQ. ID NO: 42
CAACTTTTTG GTACAAAGTT GGCA

SEQ. ID NO: 43
GTTCAACTTT TTGGTACAAA GTTGT

SEQ. ID NO: 44
CAACTTTTTA ATACAAAGTT GT

SEQ. ID NO: 45
GTTCAACTTT TTAATACAAA GTTGGCA

SEQ. ID NO: 46
CAACTTTTTA ATACAAAGTT GGCA

SEQ. ID NO: 47
GTTCAACTTT TTAATACAAA GTTGT

SEQ. ID NO: 48
Pro-Ala-Phe-Leu-Tyr-Lys-Val-Gly-Ile-Ile-Arg-Lys-
His-Cys-Leu-Ser-Ile-Cys-Cys-Asn-Glu-Gln-Val-Thr-
Ile-Ser-Gln-Asn-Lys-Ile-Ile-Ile

SEQ. ID NO: 49
Pro-Ala-Phe-Leu-Tyr-Lys-Val-Gly-Ile-Ile-Arg-Lys-
His-Cys-Leu-Ser-Ile-Cys-Cys-Asn-Glu-Gln-Val-Thr-
Ile-Ser-Gln-Asn-Lys-Ile-Ile-Ile

BRIEF DESCRIPTION OF THE DRAWINGS

FIG. 17 shows differential binding of biarsenicals to tetracysteine sequences. SlyD+His tag and ACP proteins were purified, mixed together, labeled with the indicated biarsenical molecule, and electrophoresed. The gel was imaged using a Fuji Film FLA 5000 laser scanner.

DETAILED DESCRIPTION OF THE INVENTION

Figure 1:
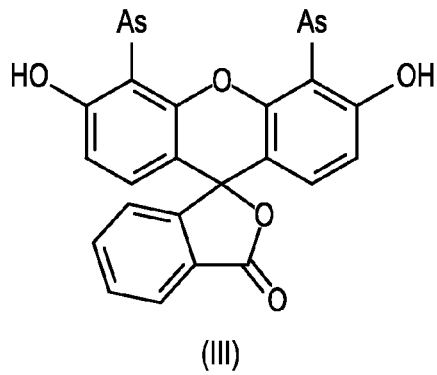
FIG. 1 illustrates pairs of biarsenical molecules that are tautomers, salts or anhydrides of each other.
Figure 1:
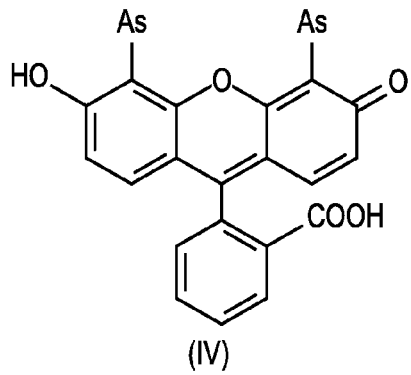
Figure 1:
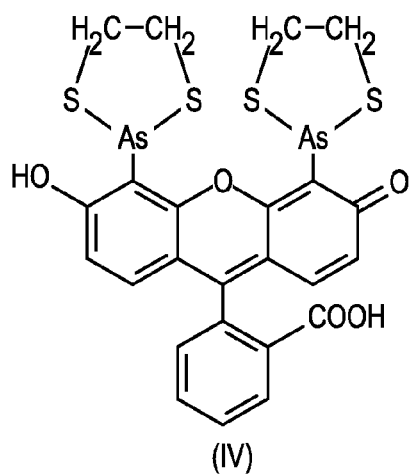
Figure 1:
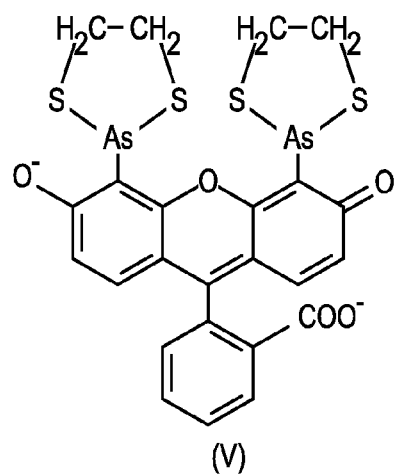
Figure 1:
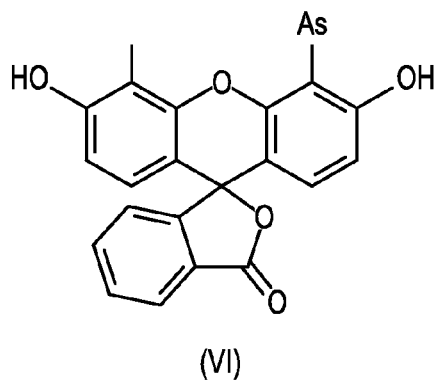
Figure 1:
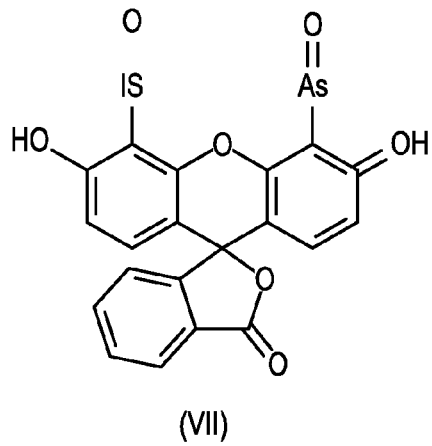
Figure 2A:
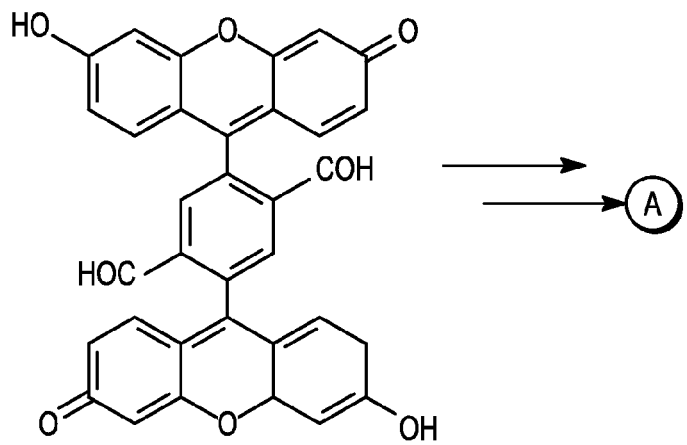
FIGS. 2A-2B is a reaction scheme for the synthesis of tetraarsenical molecules.
Figure 2A:
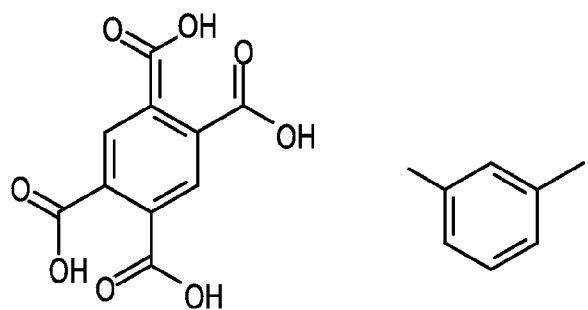
Figure 2A:
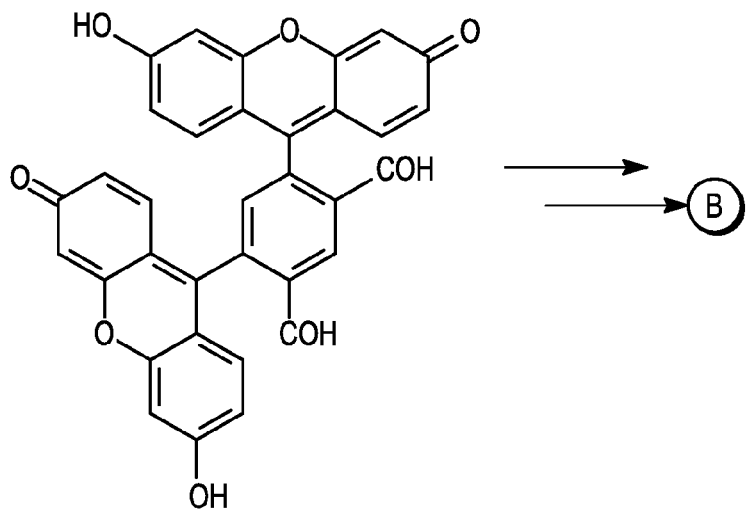
Figure 2B:
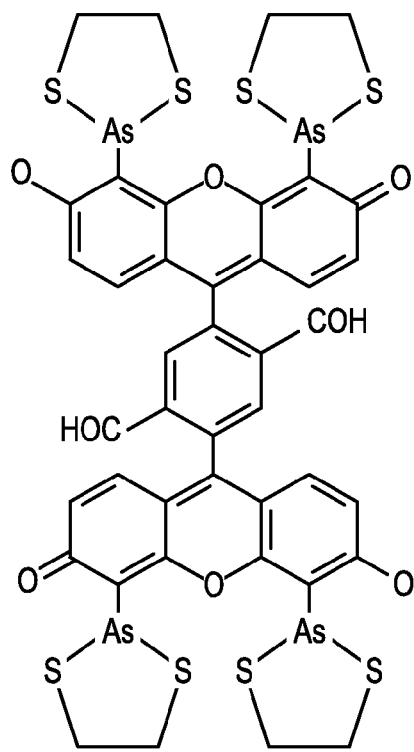
Figure 2B:
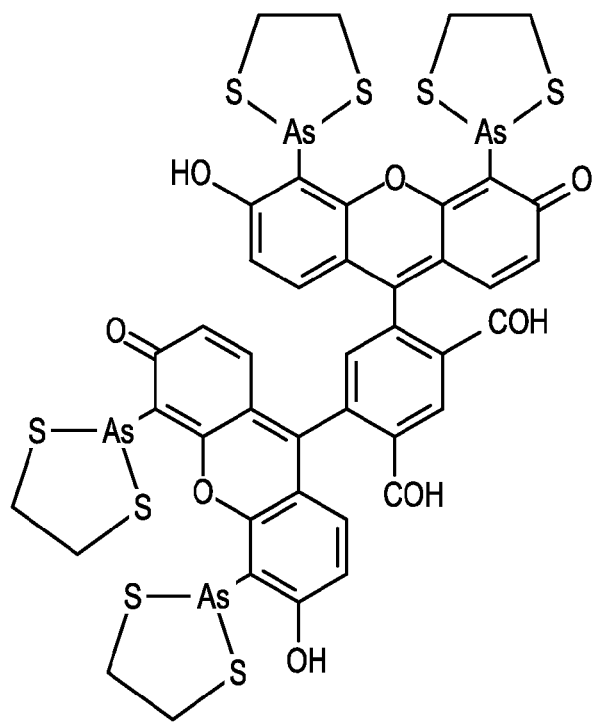
Figure 3:
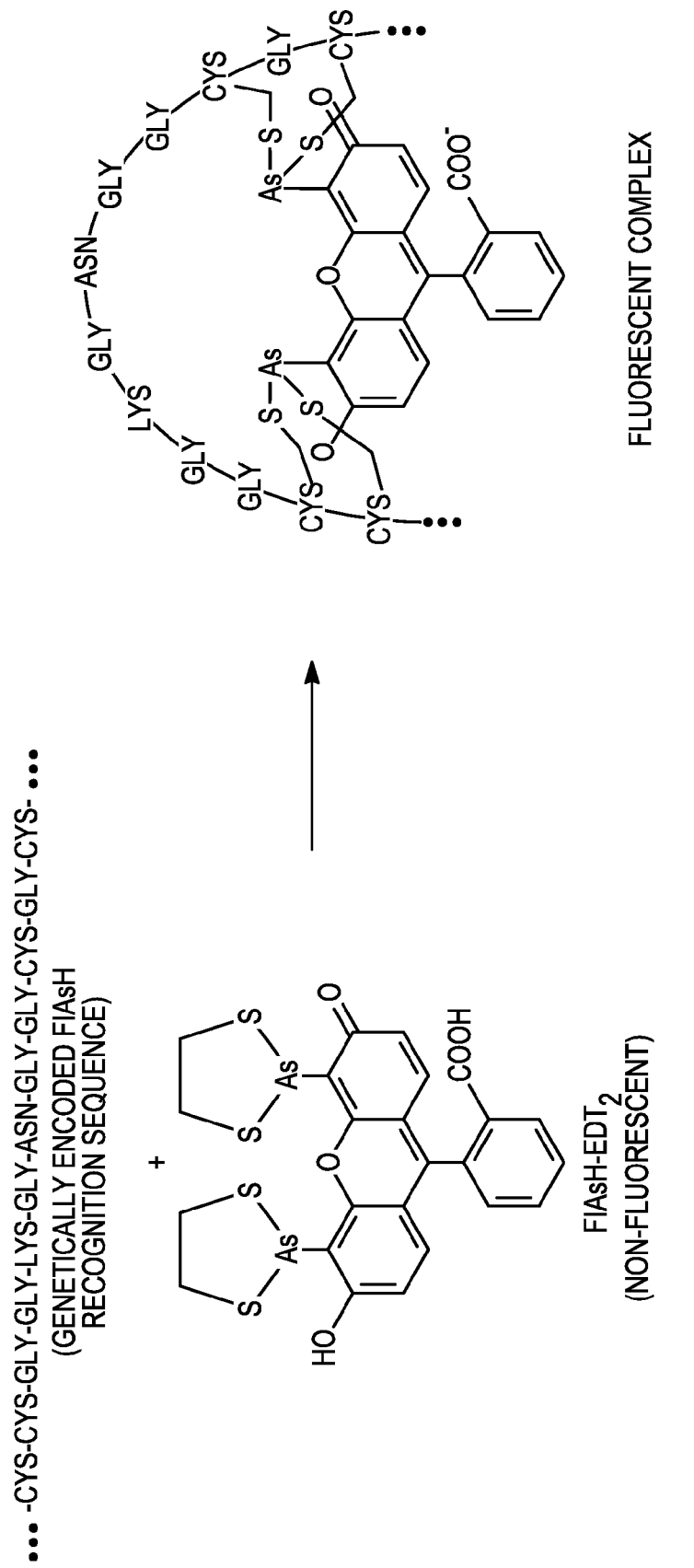
FIG. 3 illustrates a reaction scheme for binding a target sequence to a biarsenical molecule.
Figure 4:
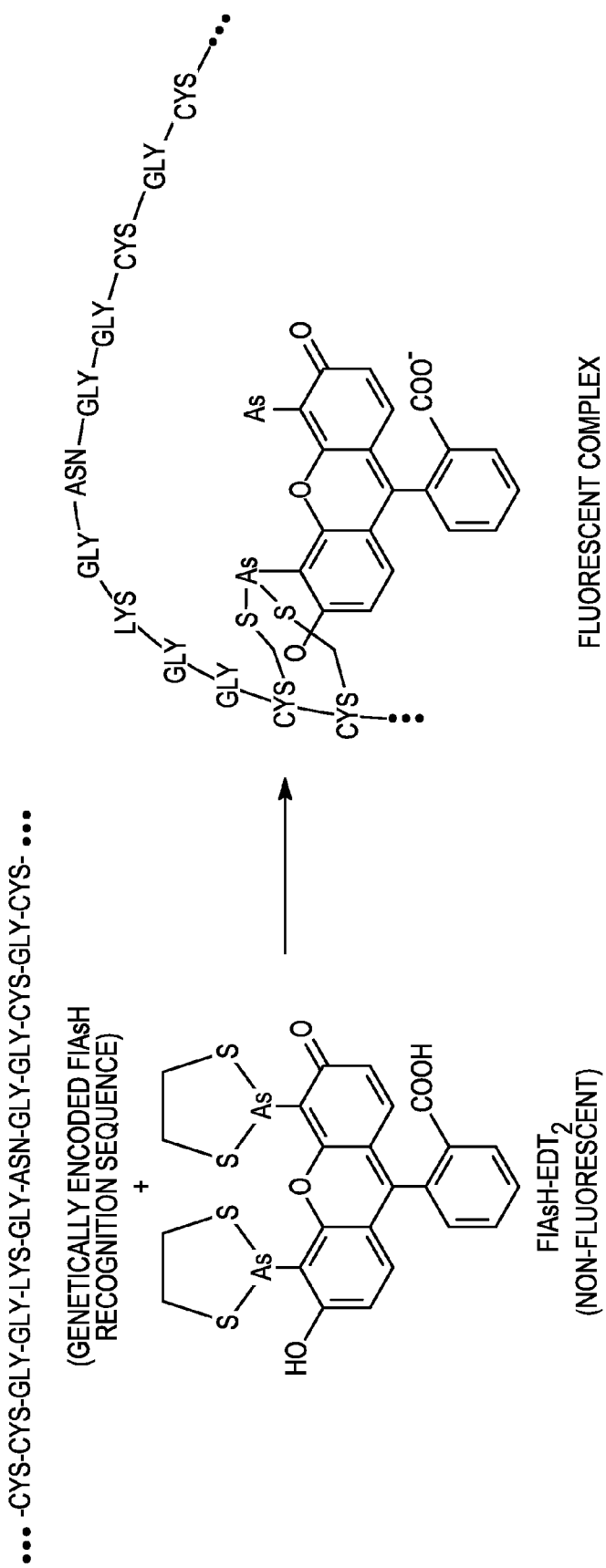
FIG. 4 illustrates a reaction scheme for binding a target sequence to a biarsenical molecule.
Figure 5:
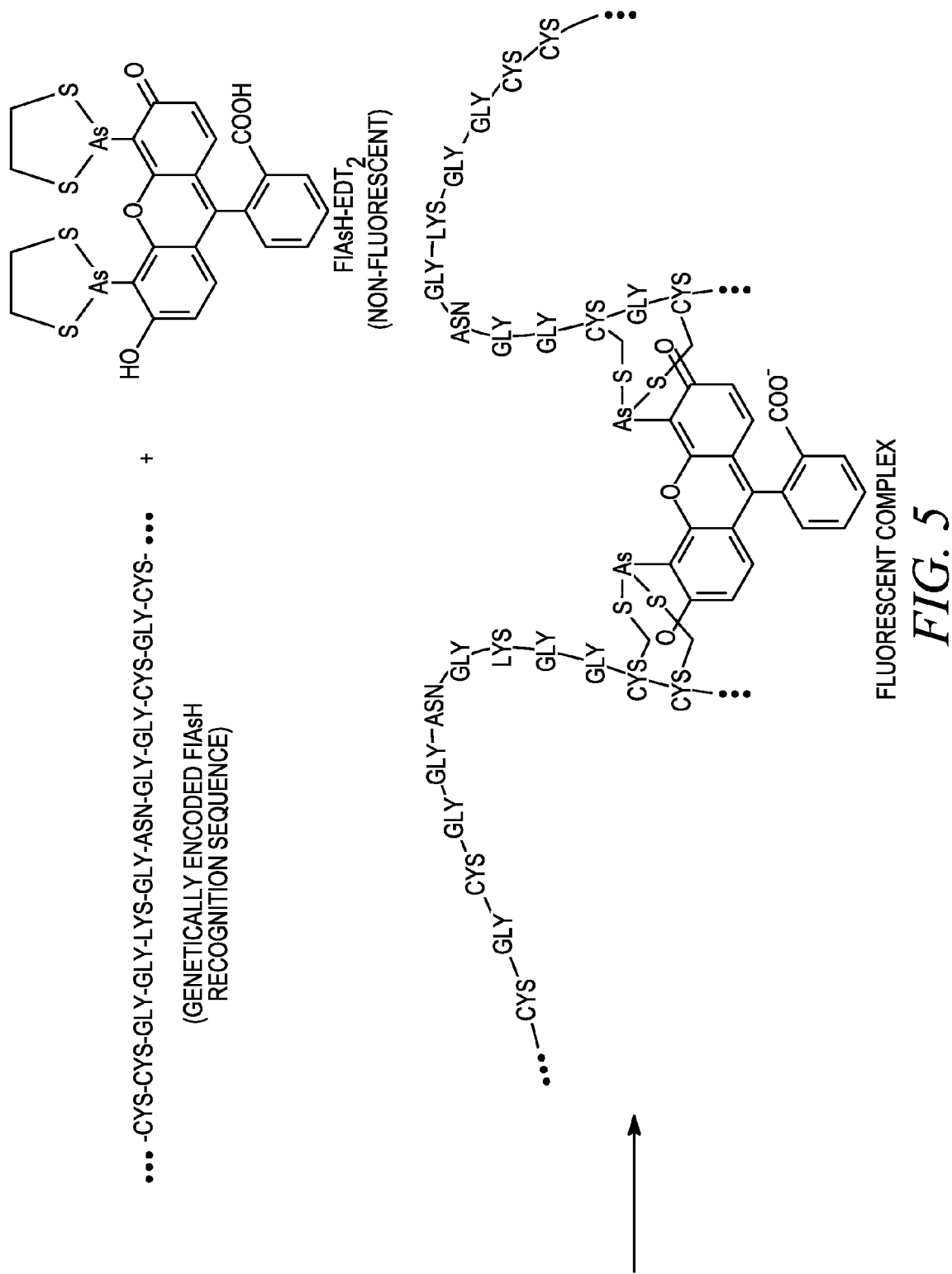
FIG. 5 illustrates a reaction scheme for binding a target sequence to a biarsenical molecule.

In one embodiment, the invention provides vectors including a nucleic acid sequence encoding a bonding partner, wherein the nucleic acid sequence encoding the bonding partner includes a nucleic acid sequence encoding a carrier polypeptide and a nucleic acid sequence encoding a target sequence, wherein the nucleic acid sequence encoding the target sequence is heterologous to the nucleic acid sequence encoding the carrier polypeptide, and the target sequence comprises at least 2 cysteines and has the sequence of Cys-Cys-R$_n$, whether R is any amino acid and n is an integer from 1-100, and wherein when n≥2, each R is selected independently from every other R in the sequence, but wherein the target sequence cannot be Cys-Cys-Xaa-Xaa-Cys-Cys (SEQ. ID NO: 1) wherein Xaa can be any amino acid, and wherein the target sequence reacts with a biarsenical molecule having the formula:

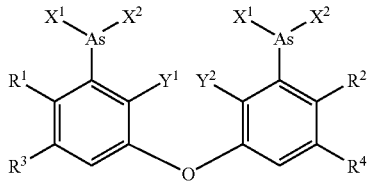

and tautomers, anhydrides, and salts thereof;
wherein:
each $X^1$ or $X^2$ is independently Cl, Br, I, OR$^a$, or SR$^a$, or $X^1$ and $X^2$ together with the arsenic atom form a ring having the formula:

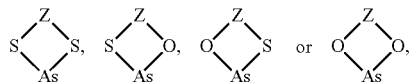

R$^a$ is H, C$_1$-C$_4$ alkyl, CH$_2$CH$_2$OH, CH$_2$COOH, or CN;
Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;
$Y^1$ and $Y^2$, are each independently H or CH$_3$, or
$Y^1$ and $Y^2$ together form a ring such that the biarsenical molecule has the formula

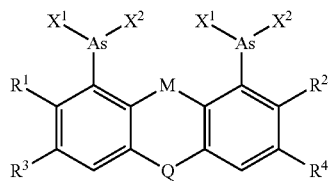

wherein:
M is O, S, CH$_2$, C(CH$_3$)$_2$, or NH;
$R^1$ and $R^2$ are each independently OR$^a$, OAc, NR$^a$R$^b$, or H;
$R^3$ and $R^4$ are each independently H, F, Cl, Br, I, OR$^a$, or R$^a$; or
$R^1$ together with $R^3$, or $R^2$ together with $R^4$, or both, form a ring in which
(i) one of $R^1$ or $R^3$ is C$_2$-C$_3$ alkyl and the other is NR$^a$ and
(ii) one of $R^2$ and $R^4$ is C$_2$-C$_3$ alkyl and the other is NR$^a$;
$R^b$ is H, C$_1$-C$_4$ alkyl, CH$_2$CH$_2$OH, CH$_2$COOH, or CN;
Q is CR$^a$R$^b$, CR$^a$OR$^b$, C=O, or a spirolactone having the formula:

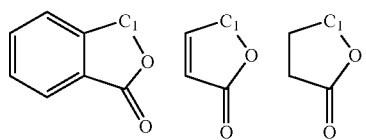

wherein the spiro linkage is formed at C$_1$.

In a preferred embodiment, n is an integer from 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, or 1-100. In another preferred embodiment, when N is greater than or equal to 2, the target sequence contains at least 4 cysteine residues.

As used herein, the term "vector" refers to a plasmid, virus or other vehicle known in the art that has been manipulated by insertion or incorporation of a nucleic acid sequence. Useful polypeptides may also be generated by nucleic acid techniques involving expression of nucleic acid sequences that encode the polypeptides.

As used herein, the phrase "bonding partner" refers to a molecule that contains at least the target sequence.

As used herein, the term "heterologous" refers to two molecules that are not naturally associated with each other.

As used herein, the term "reacts" means that the target sequence and the biarsenical molecules interact either covalently or non-covalently.

Target sequences contemplated for use in the practice of the invention include, but are not limited to, tetracysteine sequences, as set forth below:

Cys-Cys-X-X-X-X-X-X-Cys-X-Cys-X, (SEQ. ID NO: 2)

wherein X can be any amino acid, including cysteine.

An exemplary target sequence is set forth as follows: Cys-Cys-X$_1$-X$_1$-X$_2$-X$_1$-X$_3$-X$_1$-X$_1$-Cys-X$_1$-Cys-X$_2$ (SEQ. ID NO: 3), wherein X$_1$ is an amino acid having a non-polar side chain, X$_2$ is an amino acid having a basic side chain, and X$_3$ is an amino acid having a non-ionic polar side chain. In some embodiments, X$_1$ is glycine, alanine, valine, leucine, isoleucine, methionine, proline, phenylalanine, or tryptophan. In other embodiments, X$_2$ is lysine, arginine, or histidine. In still further embodiments, X$_3$ is asparagine, glutamine, serine, or threonine.

An exemplary target sequence contemplated for use in the practice of the invention is Cys-Cys-Gly-Gly-Lys-Gly-Asn-Gly-Gly-Cys-Gly-Cys-His (SEQ. ID. NO. 50), as well as variants thereof that retain reactivity with the biarsenical molecule. In this target sequence, the N-terminus is acetylated and the C-terminus is amidated. A target sequence that is not acetylated and amidated at the N- and C-terminus is also within the scope of this invention. "Variant" target sequences contain one or more amino acid substitutions, typically with amino acid substitutes of approximately the same charge and polarity. Such substitutions can include, e.g., substitutions within the following groups: valine, isoleucine, leucine, methionine; aspartic acid, glutamic acid; asparagine, glutamine; serine, threonine; lysine, arginine; and phenylalanine, tyrosine. In general, such substitutions do not significantly affect the function of a polypeptide. Methods for producing target sequences include molecular biology methods and chemical polypeptide synthesis methods.

The target sequence alone may be able to react with the biarsenical molecule. The target sequence can vary in size. In a preferred embodiment, the target sequence contains at least 10 amino acids. Preferably, the target sequence is at least 13 amino acids. Alternatively, the target sequence may only adopt an appropriate configuration when it is associated with a carrier molecule. For example, the biarsenical molecule may react with a target sequence only when the target sequence is placed in an α-helical domain of a polypeptide. It is also contemplated that the biarsenical molecule may bind a pair of target sequences as shown, for example, in FIG. 13.

The target sequence alone may not be completely helical under the reaction conditions. For example, reaction of a first arsenic with two cysteines may position other cysteines favorably for reacting with the other arsenic of the biarsenical molecule.

A target sequence containing secondary structures is also within the scope of this invention. For example, A tetracysteine target sequence may be within a β-sheet structure. Other secondary structures are possible as long as the target sequence can react with the biarsenical molecule.

The bonding partner includes a target sequence, preferably containing 2 cysteines, more preferably containing 4 cysteines, that reacts with the biarsenical molecule. In addition to the target sequence, the bonding partner may also include a carrier molecule that is associated with the target sequence. Examples of carrier molecules include polypeptides, nucleic acids, sugars, carbohydrates, lipids, natural polymers, synthetic polymers, and other biologically or chemically active molecules.

In some embodiments, the carrier molecule can be a polypeptide. In such cases, the polypeptide is referred to as a carrier polypeptide. In these embodiments, the bonding partner includes the carrier polypeptide that is associated with the target sequence. A "polypeptide bonding partner" as used herein refers to a bonding partner that includes a carrier polypeptide and a target sequence. The carrier polypeptide can be any polypeptide of interest. Examples of carrier polypeptides include antibodies, receptors, hormones, enzymes, binding proteins, and fragments thereof.

The target sequence and the carrier polypeptide may be associated with each other covalently. Alternatively, the carrier polypeptide and the target sequence may be non-covalently associated.

The position of the target sequence with respect to the carrier polypeptide can vary in a bonding partner. The target sequence may be attached to the C-terminal end of the carrier polypeptide. Alternatively, the target sequence may be attached to the N-terminal end of the carrier polypeptide.

The target sequence may also be internal to the carrier polypeptide. An internal target sequence may be produced by inserting the target sequence at an internal site in the carrier polypeptide. Alternatively, an internal target sequence may be created by modifying one or more amino acids of the polypeptide to create a target sequence. Such internal sites are typically selected for their α-helical structures. Computer algorithms and X-ray crystallography data can be used to identify α-helical structures within polypeptides.

In some embodiments, the target sequence and the carrier polypeptide are heterologous to each other. The carrier polypeptide and the target sequence are also heterologous if the amino acid sequence of the carrier polypeptide is altered at one or more amino acid positions to generate the target sequence.

Any of the polypeptides and/or target sequences used in the invention, collectively referred to herein as "polypeptides", can be synthesized by such commonly used methods as t-BOC or FMOC protection of α-amino groups. Both methods involve stepwise syntheses whereby a single amino acid is added at each step starting from the C terminus of the peptide (See, Coligan, et al., Current Protocols in Immunology, Wiley Interscience, 1991, Unit 9). Polypeptides may also be synthesized by the well known solid phase peptide synthesis methods described in Merrifield, (J. Am. Chem. Soc., 85:2149, 1962), and Stewart and Young, Solid Phase Peptides Synthesis, (Freeman, San Francisco, 1969, pp. 27-62), using a copoly(styrene-divinylbenzene) containing 0.1-1.0 niMol amines/g polymer. On completion of chemical synthesis, the polypeptides can be deprotected and cleaved from the polymer by treatment with liquid HF-10% anisole for about ¼-1 hours at 0° C. After evaporation of the reagents, the polypeptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous polypeptide or polypeptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Polypeptides may also be produced by the "native chemical" ligation technique which links together polypeptides (Dawson et al., Science, 266:776, 1994). Protein sequencing, structure and modeling approaches for use with a number of the above techniques are disclosed in Protein Engineering, loc. cit., and Current Protocols in Molecular Biology, Vols. 1 and 2, supra.

The polypeptides can also be non-polypeptide compounds that mimic the specific reaction and function of a polypeptide ("mimetics"). Mimetics can be produced by the approach outlined in Saragovi et al., Science, 253:792-795 (1991). Mimetics are molecules which mimic elements of polypeptide secondary structure. See, for example, Johnson et al., "Peptide Turn Mimetics", in Biotechnology and Pharmacy, Pezzuto et al., Eds., (Chapman and Hall, New York 1993). The underlying rationale behind the use of peptide mimetics is that the peptide backbone exists chiefly to orient amino acid side chains in such a way as to facilitate molecular interactions. For the purposes of the present invention, appropriate mimetics can be considered to be the equivalent of any of the polypeptides used in the invention.

Methods that are well known in the art can be used to construct vectors according to the invention, including in vitro recombinant DNA techniques, synthetic techniques, and in vivo recombination/genetic techniques. (See, for example, the techniques described in Maniatis et al. 1989 Molecular Cloning A Laboratory Manual, Cold Spring Harbor Laboratory, N.Y.)

Suitable vectors include T7-based expression vectors for expression in bacteria (Rosenberg, et al., Gene, 56:125, 1987), the pMSXND expression vector for expression in mammalian cells (Lee and Nathans, J. Biol. Chem., 263: 3521, 1988) and baculovirus-derived vectors for expression in insect cells. Retroviral vectors may also be used. Examples of retroviral vectors include Moloney murine leukemia virus, (MoMuLV), Harvey murine sarcoma virus (HaMuS-V), murine mammary tumor virus (MuMTV), and Rous Sarcoma Virus (RSV). Expression vectors suitable for in vitro expression may also be used.

Generally, the vector includes a nucleic acid sequence encoding the target sequence. Typically, the nucleic acid sequence is a DNA sequence, although the nucleic acid can be an RNA sequence. The nucleic acid sequence can be any sequence that encodes a target sequence capable of reaching with the biarsenical molecule. This can include nucleic acid sequences that are degenerate variants of each other. By "degenerate variants" is meant nucleic acid sequences that encode the same amino acid sequence, but in which at least one codon in the nucleotide sequence is different. Degenerate variants occur due to the degeneracy of the genetic code, whereby two or more different codons can encode the same amino acid. Nucleic acid sequences of the present invention may be synthetic.

The vector may also contain a nucleic acid sequence encoding a carrier polypeptide, in addition to the nucleic acid sequence encoding the target sequence. Nucleic acid sequences encoding the carrier polypeptide and the target sequence can form a recombinant gene that, when expressed, produces a polypeptide bonding partner.

The nucleic acid sequence encoding the target sequence can be on the 5' or 3'-end of the nucleic acid sequence encoding the carrier polypeptide. Alternatively, the nucleic acid sequence encoding the target sequence can be internal to the nucleic acid sequence encoding the carrier polypeptide. In such a case, the nucleic acid sequence encoding the target sequence can be spliced into an internal site of the nucleic acid sequence encoding the carrier polypeptide. In this case, the nucleic acid sequence encoding the target sequence is flanked by nucleic acid sequences encoding the carrier polypeptide.

The nucleic acid sequence encoding the carrier polypeptide may contain an appropriate restriction enzyme site within its nucleic acid sequence that can be used for inserting the nucleic acid sequence encoding the target sequence. Alternatively, an appropriate restriction enzyme site can be engineered in the nucleic acid sequence encoding the carrier polypeptide at a desired location. A restriction enzyme site may be engineered by any number of known methods.

The nucleic acid sequence encoding the carrier polypeptide may by altered at one or more positions to generate the nucleic acid sequence that encodes the target sequence. In some embodiments, changes in the nucleic acid sequence encoding the carrier polypeptide may be made to generate a nucleic acid encoding a target sequence without substantially affecting the function of the carrier polypeptide.

Site-specific and region-directed mutagenesis techniques, as well as standard recombinant techniques can be employed for generating some of the nucleic acid sequences that encode the polypeptides used in the invention. See Current Protocols in Molecular Biology, Vol. 1, Ch. 8 (Ausubel et al., eds., J. Wiley & Sons 1989 & Supp. 1990-93); Protein Engineering (Oxender & Fox eds., A. Liss, Inc. 1987). In addition, linker-scanning and PCR-mediated techniques can be employed for mutagenesis. See PCR Technology (Erlich ed., Stockton Press 1989); Current Protocols in Molecular Biology, Vols. 1 & 2, supra.

The vector may also contain any number of regulatory elements for driving expression of the polypeptides. Nucleic acid sequences encoding polypeptides may be operatively associated with a regulatory element. Regulatory elements include, but are not limited to, inducible and non-inducible promoters, enhancers, operators and other elements that drive or otherwise regulate gene expression.

Typically, a nucleic acid sequence encoding a polypeptide is operatively linked to a promoter that is active in the appropriate environment, i.e. a host cell. A variety of appropriate promoters are known in the art and may be used in the present invention. The promoter may be a promoter that naturally drives expression of the carrier polypeptide. The promoter may be a viral promoter, a bacterial promoter, a yeast promoter, insect promoter or a plant promoter, and can be host cell-specific. Examples of promoters include, without limitation, T7, metallothionein I, or polyhedron promoters. For example, if the polypeptides will be expressed in a bacterial system, inducible promoters such as pL of bacteriophage gamma, plac, ptrp, ptac (trp-lac hybrid promoter) and the like may be used. In mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used.

The vector may also include enhancer sequences. Enhancer sequences can be placed in a variety of locations in relation to polypeptide-encoding nucleic acid sequences. For example, enhancer sequences can be placed upstream or downstream of the coding sequences, and can be located adjacent to, or at a distance from, the polypeptide encoding nucleic acid sequences.

The vector may also contain a nucleic acid sequence encoding a selectable marker for use in identifying host cells containing a vector. A selectable marker in a vector typically confers some form of drug or antibiotic resistance to the host cells carrying the vector.

A number of selection systems may be used. In bacterial host cells, a number of antibiotic markers may be used. Antibiotic markers include tetracycline, ampicillin, and kanamycin. In mammalian host cells, selections systems include, but are not limited to herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817). Also, antimetabolite resistance can be used as the basis of selection for dhfr, which confers resistance to methotrexate (Wigler, et al., 1980, Proc. Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78:2072; neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30: 147) genes. Additional selectable genes include, trpB, which allows cells to utilize indole in place of tryptophan; hisD, which allows cells to utilize histinol in place of histidine (Harman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

A number of dithiols may be used for bonding the arsenics. The dithiol groups may protect the biarsenical molecule from reacting with low affinity sites, for example, single cysteine residues or dihydrolipoic acid moieties. The dithiol may form a five- or six-membered ring with the arsenic. Vicinal dithiols that form five membered rings are preferable. Typically, the five-membered rings may be more stable. 1,3-dithiols forming six-membered rings may also be used. The dithiol may contain additional substituents to control volatility, water solubility, proton ionization constants, redox potential, and tendency to complex with the arsenic. Increasing the molecular weight may decrease volatility and odor. Polar substituents such as hydroxymethyl, carboxyl and sulfo decrease volatility and increase water solubility. However, these substituents may also decrease the ability of the biarsenical molecule to traverse a biological membrane.

Dithiols that contain rings may increase the affinity of the dithiol to the arsenic by organizing the two thiol groups to be in a cis-conformation ready to form an additional ring with the arsenic. Examples of dithiol rings are 1,2-benzenedithiol and 1,2-cyclohexanedithiol.

Preferably, each arsenic in the biarsenical molecule is bonded to a dithiol, such as 1,2-ethanedithiol (EDT). An unexpected advantage of the biarsenical molecule of formula (III) that is bonded to EDT is that it is essentially completely nonfluorescent. Biarsenical molecules that have detectable fluorescence are also within the scope of this invention.

The moiety "Q" as set forth above is preferably a spirolactone. Particularly preferable is a biarsenical molecule in which Q is a bicyclic spirolactone as in formula (III). The tautomers, anhydrides and salts of molecule (III) are also within the scope of the invention.

The biarsenical molecule may be engineered to contain a variety of detectable groups. "Detectable group" as used herein refers to any atom or molecule that can be engineered into the biarsenical molecule to aid in the detection of the biarsenical molecule without significantly destroying the biarsenical molecule's ability to react with a target sequence.

Figure 6:
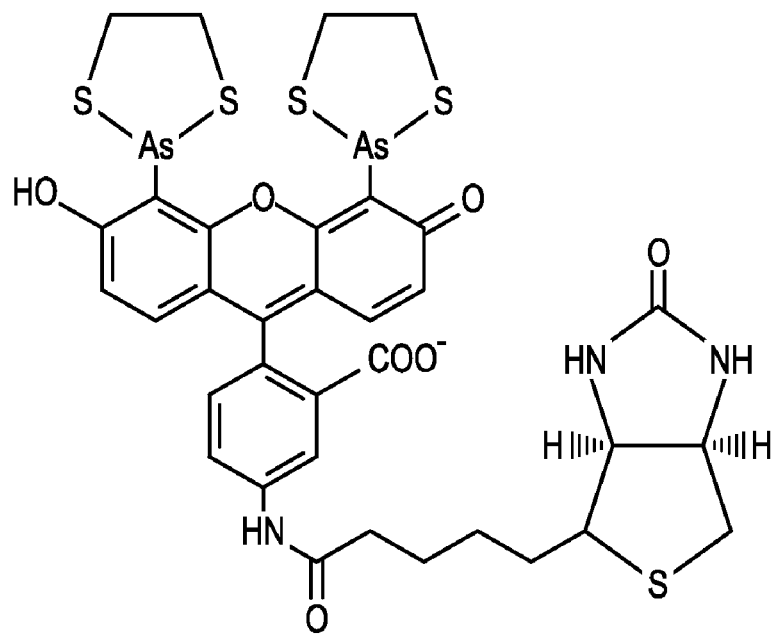
FIG. 6 illustrates biarsenical molecules with detectable groups.
Figure 6:
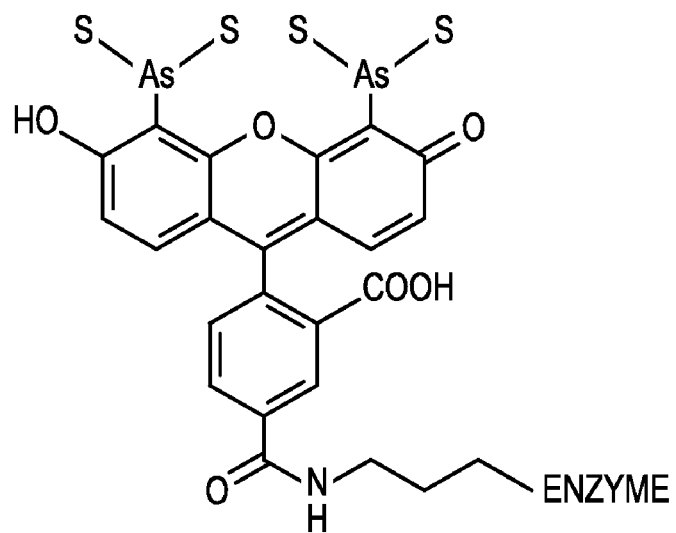
Figure 9:
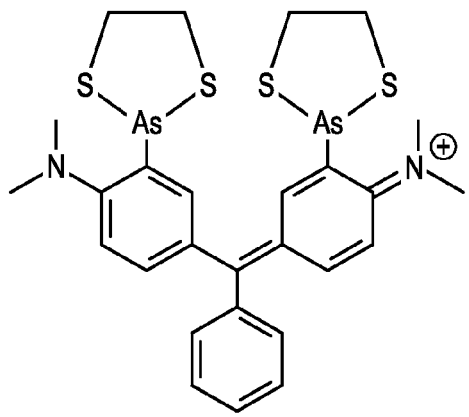
FIG. 9 illustrates biarsenical molecules with detectable groups.
Figure 9:
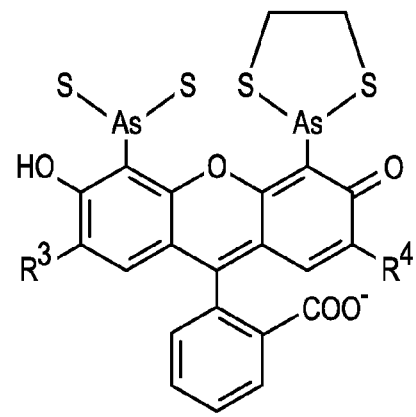
Figure 9:
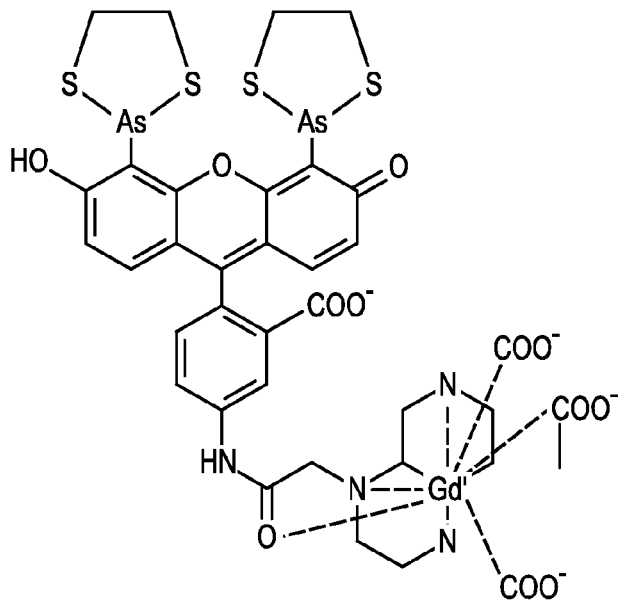
Figure 9:
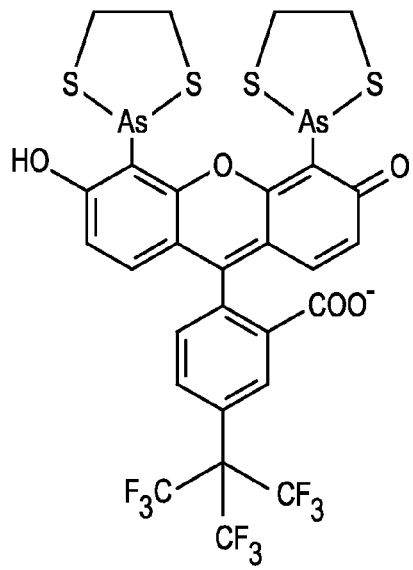
Figure 10:
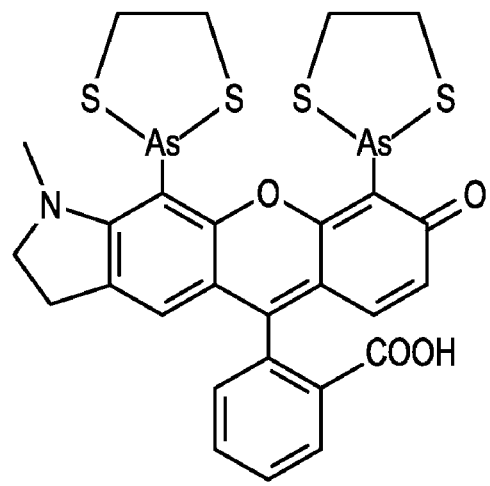
FIG. 10 illustrates a biarsenical molecule in which the fluorescent signal is sensitive to local solvent polarity.

The biarsenical molecule may be substituted at one or more positions to add a signal generating detectable group. Inclusion of more than one detectable group is also within the scope of this invention. The selection of a detectable group may be made based on the ease of the protocol for engineering the detectable group into the biarsenical molecule, and on the end use of the biarsenical molecule. Examples of detectable groups include fluorescent groups, phosphorescent groups, luminescent groups, spin labels, photosensitizers, photocleavable moieties, chelating centers, heavy atoms, radioactive isotopes, isotopes detectable by nuclear magnetic resonance, paramagnetic atoms, and combinations thereof FIGS. 6, 8 and 9 illustrate biarsenical molecules with some of abovementioned detectable groups. FIG. 10 illustrates a biarsenical molecule in which the fluorescent signal is sensitive to local solvent polarity.

Typically, a detectable group generates a detectable signal that can be readily monitored. Examples of detectable signals that can be monitored include fluorescence, fluorescence anisotropy, time-resolved luminescence, phosphorescence amplitude and anisotropy, electron spin resonance (ESR), singlet oxygen production, hydroxy radical-mediated protein inactivation, metal-ion sensing, X-ray scattering, radioactivity, nuclear magnetic resonance spectroscopy of the attached isotope, and enhanced relaxivity of protons in the immediate vicinity of a paramagnetic species.

Other modifying groups that aid in the use of the biarsenical molecule may also be incorporated. For example, the biarsenical molecule may be substituted at one or more positions to add a solid phase binding group or a cross-linking group. The biarsenical molecule may be coupled to a solid phase.

The biarsenical molecule preferably is capable of traversing a biological membrane. The small size of the biarsenical molecule can contribute toward the ability of the biarsenical molecule to traverse a biological membrane. Biarsenical molecules of less than 800 Daltons are preferable for membrane traversal.

The polarity of the biarsenical molecule can also determine the ability of the biarsenical molecule to traverse a biological membrane. Generally, a hydrophobic biarsenical molecule is more likely to traverse a biological membrane. The presence of polar groups can reduce the likelihood of a molecule to traverse a biological membrane. A biarsenical molecule that is unable to traverse a biological membrane may be derivatized. The biarsenical molecule may be derivatized by addition of groups that enable or enhance the ability of the biarsenical molecule to traverse a biological membrane. Preferably, such derivatization of the biarsenical molecule does not significantly alter the ability of the biarsenical molecule to subsequently react with the target sequence. The biarsenical molecule may also be derivatized transiently. In such instances, after traversing the membrane, the derivatizing group is eliminated to regenerate the original biarsenical molecule. Examples of derivatization methods that increase membrane traversability include esterification of phenols, ether formation with acyloxyalkyl groups, and reduction of chromophores to uncharged leuco compounds.

In some embodiments, the biarsenical molecule may be nearly or completely undetectable until it reacts with a target sequence. The biarsenical molecule (III) is nonfluorescent even though it is synthesized from a fluorescent molecule (parent fluorescein). The biarsenical molecule (III) reacts with a target sequence to form a biarsenical molecule (III)/target sequence complex that is fluorescent. Moreover, the fluorescent signal generated by this complex is red-shifted by about 20 nm relative to fluorescein. This biarsenical molecule can be particularly useful because it provides a means to specifically and accurately detect the presence of the biarsenical molecule/target sequence complex with very little background signal.

Also within the scope of this invention is a biarsenical molecule that may be detectable before and after it reacts with a target sequence to form the biarsenical molecule/target sequence complex. In such instances, it is preferable if the signal of the biarsenical molecule can be differentiated from the signal of the complex. For example, if the detectable signal of the biarsenical molecule is a fluorescent signal, it would be preferable if the fluorescence of the complex is red-shifted or blue-shifted relative to the biarsenical molecule alone.

The biarsenical molecule may also lack a detectable signal, both before and even after reacting with a target sequence. These biarsenical molecules can be useful in many techniques that do not require a detectable signal, or that use other methods of detection. These biarsenical molecules may be useful when the goal is to attach a polypeptide to a solid substrate, cross-link two polypeptides or encourage a polypeptide domain to become α-helical.

Figure 11:
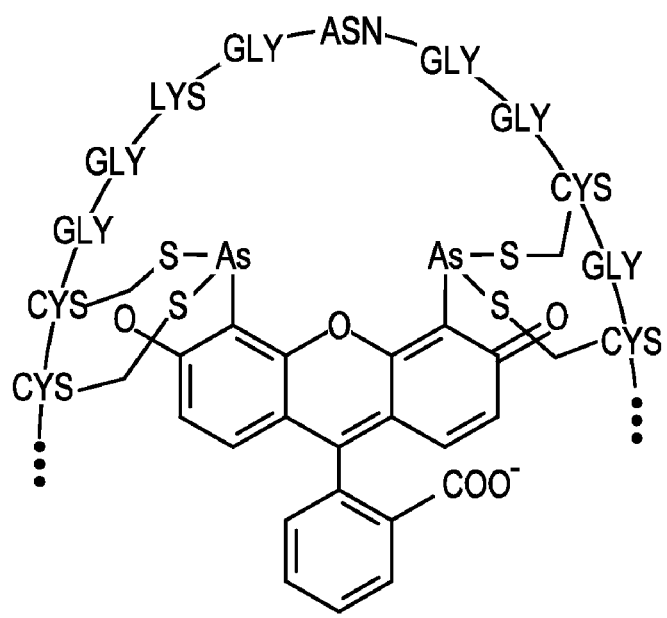
FIG. 11 illustrates a target sequence bound to a biarsenical molecule.
Figure 12:
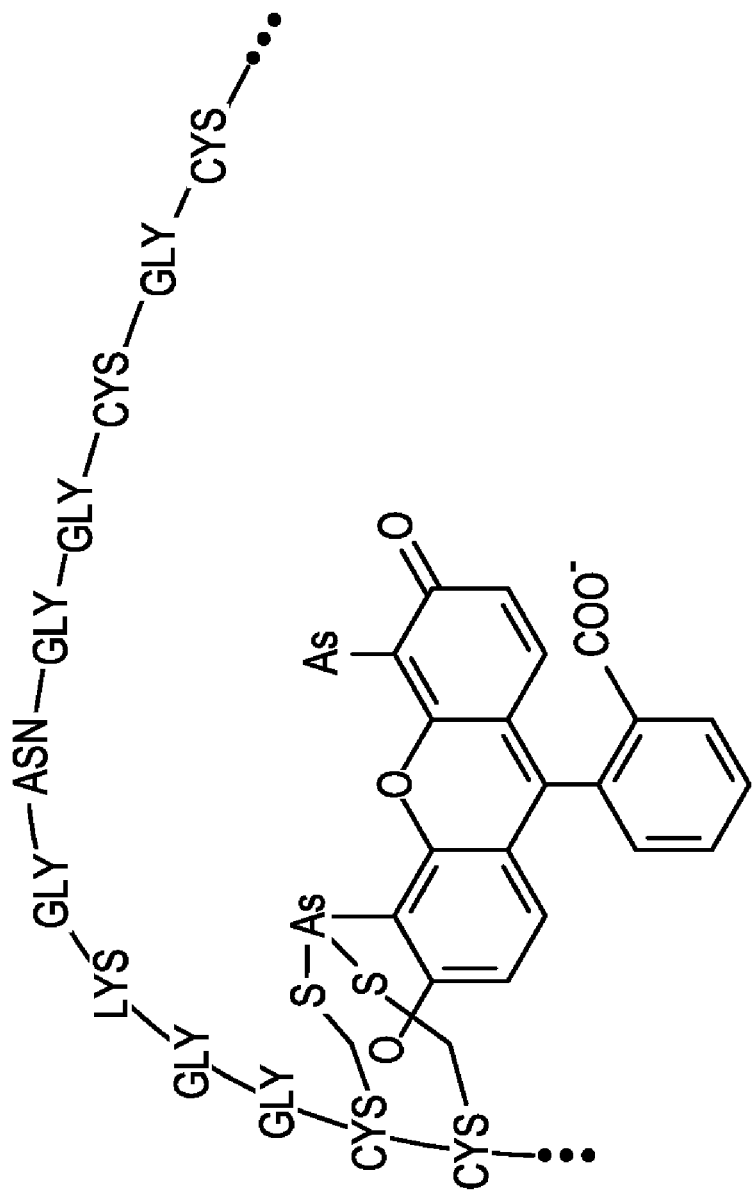
FIG. 12 illustrates a target sequence bound to a biarsenical molecule.
Figure 13:
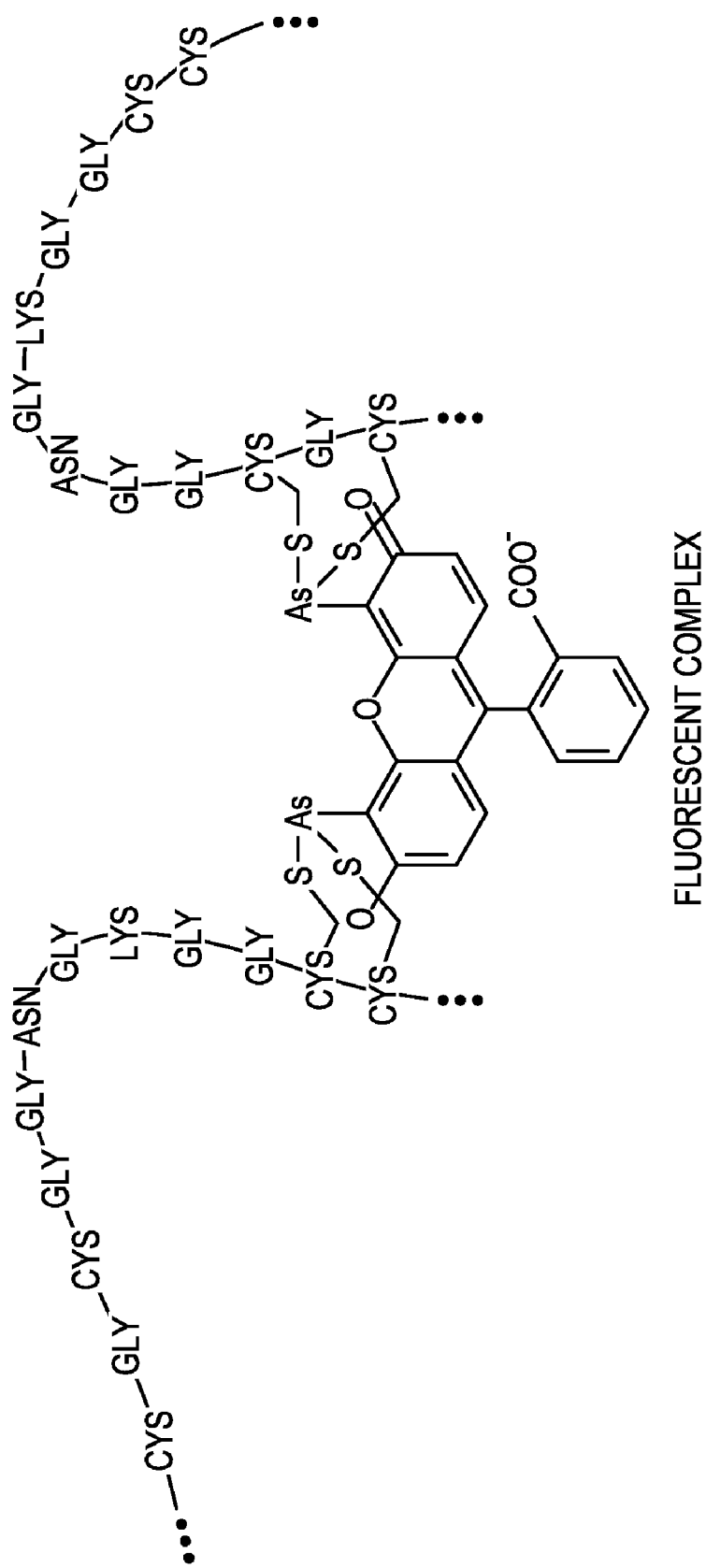
FIG. 13 illustrates multiple target sequences bound to a biarsenical molecule.

Each of the two trivalent arsenics in the biarsenical molecule may react with two cysteines. Thus, the biarsenical molecule may react with four cysteines arranged in an appropriate configuration as shown, for example, in FIG. 11. In addition, each of the two trivalent arsenics in the biarsenical molecule may react with two cysteines on different target sequences (FIG. 13). Likewise, it is also contemplated that only one arsenic in the biarsenical molecule will react with 2 cysteines on a target sequence as shown, for example, in FIG. 12.

A particularly useful advantage of the specific reaction between the biarsenical molecule and a target sequence is the reversibility of the reaction. A complex containing the biarsenical molecule and the target sequence may be dissociated. Dissociation may be accomplished by providing an excess of reagents such as EDT or other similar dithiols.

In general, the biarsenical molecule can be prepared by a short synthesis. U.S. Pat. No. 6,451,569, herein incorporated by reference, discloses the synthesis of a biarsenical molecule (III) from commercially available fluorescein mercuric acetate (FMA).

Figure 7:
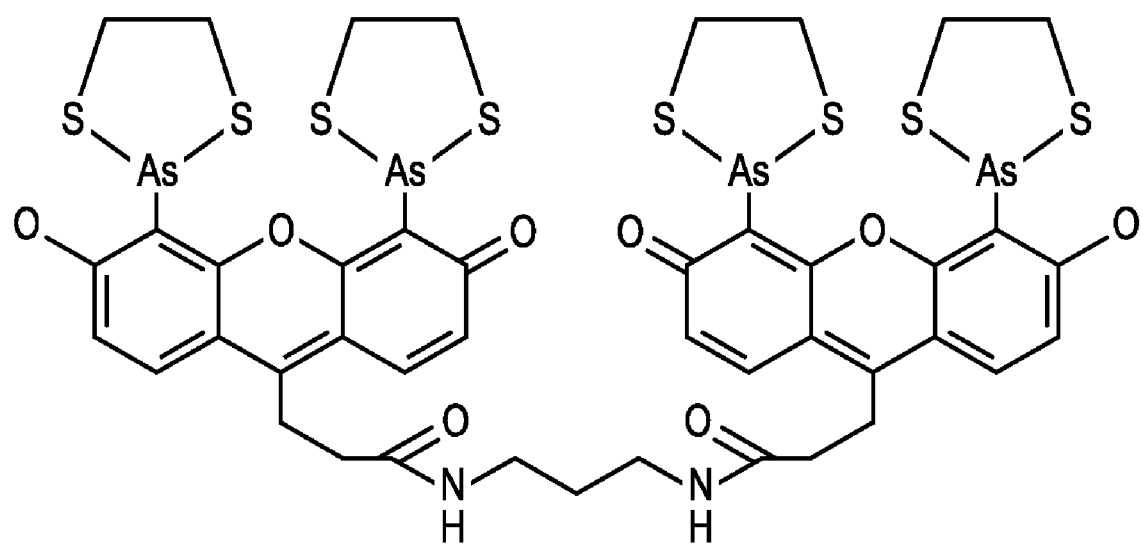
FIG. 7 illustrates the structure of a tetraarsenical molecule.
Figure 8A:
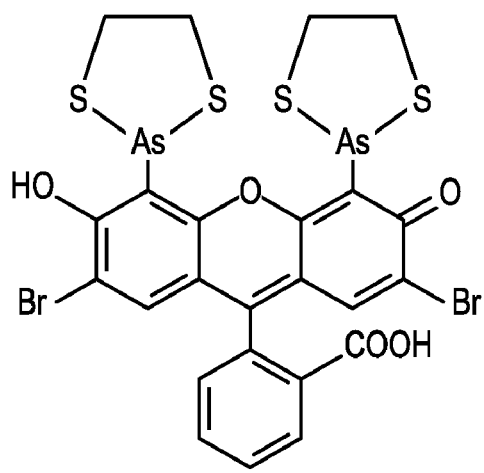
FIGS. 8A-8B illustrates biarsenical molecules with detectable groups.
Figure 8A:
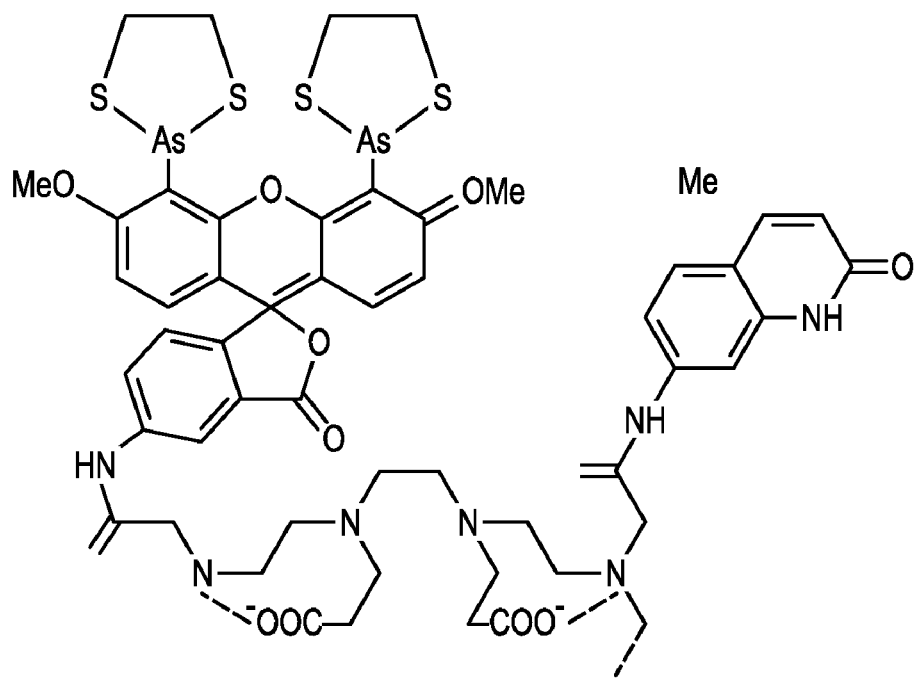
Figure 8B:
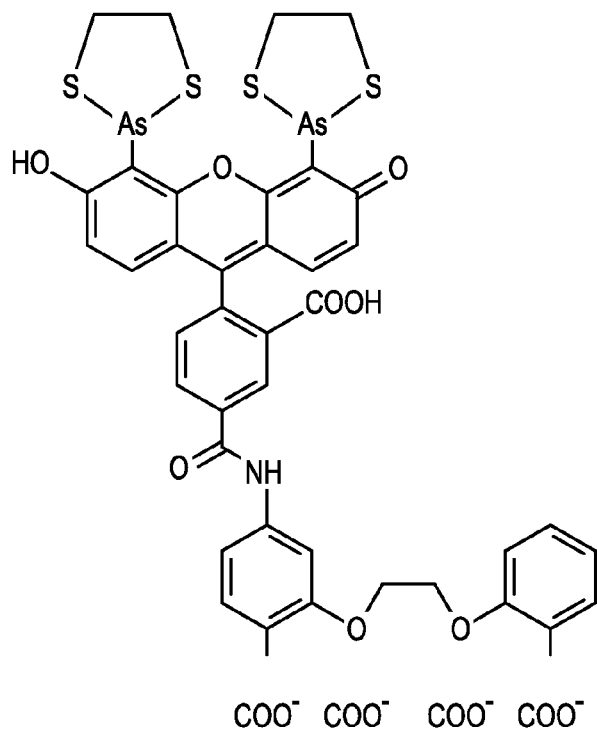
Figure 8B:
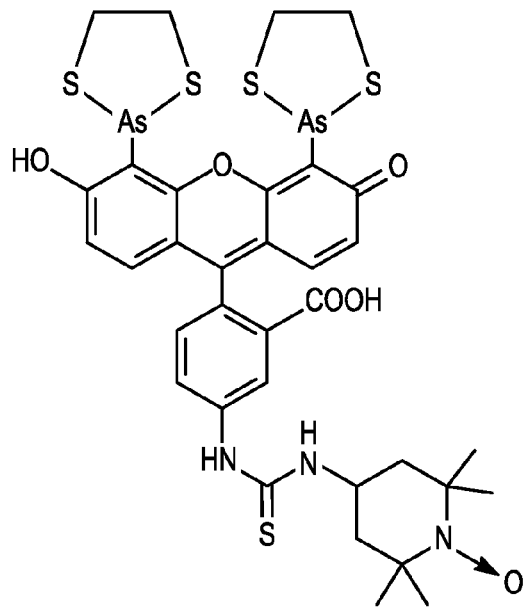

"Tetraarsenical" molecules as used herein refer to molecules that contain four arsenics. In some embodiments, tetraarsenical molecules are two biarsenical molecules chemically coupled to each other through a linking group. Tetraarsenical molecules may be synthesized in a variety of ways. FIG. 2 illustrates one scheme for synthesizing tetraarsenical molecules that have two biarsenical molecules coupled through either a para- or a meta-dicarboxylbenzene. The synthesis in FIG. 2 results in two types of molecules, a meta- and a para-substituted tetraarsenical molecule. FIG. 7 is another example of a tetraarsenical molecule coupled through a dialkylamido linking group. Other suitable linking groups include phenyl, naphthyl, biphenyl, and the like. It follows that the tetraarsenical molecule can react with two target sequences. Tetraarsenical molecules may be particularly useful as cross-linking agents, e.g., intra-molecular and intermolecular cross-linking agents.

A host cell may carry an exogenous bonding partner. "Exogenous" as used herein refers to any molecules that are introduced into a host cell. In preferred embodiments, the exogenous bonding partner is a polypeptide bonding partner.

A "host cell" can be any cell capable of carrying an exogenous bonding partner. Examples of host cells include bacterial cells, yeast cells, insect cells, mammalian cells, and plant cells. A suitable host cell type includes a cell of the following types: HeLa cells, NIH 3T3 (Murine), Mv 1 lu (Mink), BS-C-1 (African Green Monkey) and human embryonic kidney (HEK) 293 cells. Such cells are described, for example, in the Cell Line Catalog of the American Type Culture Collection (ATCC). Cells that can stably maintain a vector may be particularly advantageous. See, for example, Ausubel et al., Introduction of DNA Into Mammalian Cells, in Current Protocols in Molecular Biology, sections 9.5.1-9.5.6 (John Wiley & Sons, Inc. 1995). Preferably, host cells do not naturally express polypeptides containing target sequences that react with molecules of the invention.

An exogenous bonding partner can be introduced into a host cell by a variety of appropriate techniques. These techniques include microinjection of bonding partners and expression within a cell of nucleic acids that encode bonding partners.

A host cell can be manipulated to carry an exogenous bonding partner by introducing a nucleic acid sequence that, when expressed, produces the bonding partner. Any of the vectors described above containing a nucleic acid sequence encoding a bonding partner may be introduced into a host cell. A non-replicating nucleic acid molecule, such as a linear molecule that can express a bonding partner is also within the scope of this invention.

The expression of a desired nucleic acid molecule may occur through transient expression of the introduced polypeptide-encoding nucleic acid sequence. Alternatively, permanent expression may occur through integration of the introduced nucleic acid sequence into a host chromosome. Therefore the cells can be transformed stably or transiently. The term "host cell" may also include any progeny of a host cell. It is understood that all progeny may not be identical to the parental cell since there may be mutations that occur during replication. However, such progeny are included when the term "host cell" is used.

Typically, the vector that includes the nucleic acid sequence encoding the bonding partner is introduced into a host cell. Methods of stable transfer, meaning that the vector having the bonding partner encoding nucleic acid sequence is continuously maintained in the host, are known in the art. The vector, with appropriate regulatory elements for expression in a host cell, can be constructed as described above.

The vector may be introduced into a host cell by any conventional method, including retroviral transduction, electroporation, calcium phosphate co-precipitation, biolistics and liposome-based introduction. See, for example, Ausubel et al., Introduction of DNA Into Mammalian Cells, in CURRENT PROTOCOLS IN MOLECULAR BIOLOGY (John Wiley & Sons, Inc. 1995).

A variety of host cell-specific expression vector systems may be utilized to express polypeptides in a host cell. These include microorganisms such as bacteria transformed with recombinant bacteriophage DNA, plasmid DNA or cosmid DNA expression vectors; yeast transformed with recombinant yeast expression vectors; plant cell systems infected with recombinant virus expression vectors (e.g., cauliflower mosaic virus, CAMV; tobacco mosaic virus, TMV) or transformed with recombinant plasmid expression vectors (e.g., Ti plasmid); insect cell systems infected with recombinant virus expression vectors (e.g., baculovirus); or animal cell systems infected with recombinant virus expression vectors (e.g., retroviruses, adenovirus, vaccinia virus), or transformed animal cell systems engineered for stable expression. Polypeptides may require translational and/or post-translational modifications such as addition of carbohydrates. These modifications can be provided by a number of systems, e.g., mammalian, insect, yeast or plant expression systems.

Eukaryotic systems, and preferably mammalian expression systems, allow for proper post-translational modifications of expressed mammalian polypeptides to occur. Eukaryotic cells which possess the cellular machinery for proper processing of the primary transcript, glycosylation, phosphorylation, and advantageously, plasma membrane insertion of a polypeptide may be used as host cells.

Depending on the host cell and the vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology, 153:516-544) as described earlier. Selection of the appropriate transcription and translation elements are readily apparent to a person of ordinary skill in the art.

Vectors based on bovine papilloma virus which have the ability to replicate as extrachromosomal elements may be of particular interest (Sarver et al., 1981, Mol. Cell. Biol. 1:486). Shortly after entry of this DNA, the plasmid replicates to about 100 to 200 copies per cell. Transcription of the polypeptide encoding nucleic acid sequences does not require integration of the plasmid into the host's chromosome, thereby yielding a high level of expression. These vectors can be used for stable expression by including a selectable marker in the plasmid, such as, for example, the neo gene.

Factors of importance in selecting a particular expression system include: the ease with which a host cell that contains the vector may be recognized and selected from a host cell that does not contain the vector; the number of copies of the vector which are desired in a particular host cell; and whether it is desirable to be able to "shuttle" the vector between different types of host cells.

The biarsenical molecule, in combination with the target sequences set forth herein, form biarsenical molecule/target sequence complexes that is useful in a variety of ways. The complex is particularly useful in methods for labeling a carrier molecule. The carrier molecule can be associated with the target sequence to form a bonding partner. The bonding partner may be produced by any method, including a number of the above-described methods. In preferred embodiments, the carrier molecule is a polypeptide.

In addition, since the target sequences set forth herein react with biarsenical molecules with high specificity, the invention provides methods for orthogonally labeling a single protein or tetracysteine protein mixture. The present invention is also useful in creating stable mammalian cell lines expressing a tetracysteine tagged protein, which can overcome toxicity associated with native tetracysteine.

A bonding partner that includes a target sequence is contacted with the biarsenical molecule. Contact of the biarsenical molecule with the bonding partner is performed under conditions appropriate for a specific reaction to occur between the biarsenical molecule and the target sequence to form the biarsenical molecule/target sequence complex.

A biarsenical molecule/target sequence complex that generates a detectable signal may be used if detection of a labeled carrier molecule is desired. A particular advantage of using the biarsenical molecule and the target sequence for labeling is the specificity and the reversibility of the interaction. The biarsenical molecule/target sequence complex may be dissociated, for example, after the detection of the complex.

The biarsenical molecule may be added to a composition that includes the target sequence. The biarsenical molecule may or may not be capable of traversing a membrane. The bonding partner may be, for example, in a test tube, a microtiter well or immobilized on a solid phase or support. Additional uses of the biarsenical molecule/target sequence complex include polypeptide purification, immunoassays, and other biological and chemical assays.

Immobilization of either the biarsenical molecule or the bonding partner to a solid phase may be particularly useful. Immobilization may include adsorption, absorption or covalent bonding. A solid phase may be inert or it may be reactive for coupling. Solid phases that may be used include glass, ceramics, and natural or synthetic polymeric materials. Examples of polymeric materials include cellulose-based materials, dextran-based materials, and polystyrene-based materials.

The invention further includes methods for immobilizing molecules (e.g., peptides or proteins comprising target sequences) on solid supports, as well as methods for preparing compositions comprising molecules bound to molecules solid supports. Thus, in one aspect the invention includes contacting and/or binding a peptide or protein comprising a target sequence to a solid support and, optionally, inducing release of that molecule from the solid support. Thus, the invention also includes methods of purifying and/or isolating molecules comprising one or more target sequences by binding these molecules to a solid support; optionally, washing the solid support to remove unbound materials; inducing release of the bound molecules; and collecting the released molecules.

Solid supports which may be used in the practice of the invention include beads (e.g., silica gel, controlled pore glass, magnetic, Sephadex/Sepharose, cellulose), flat surfaces or chips (e.g., glass fiber filters, glass surfaces, metal surface (steel, gold, silver, aluminum, copper and silicon), capillaries, plastic (e.g., polyethylene, polypropylene, polyamide, polyvinylidenedifluoride membranes or microtiter plates); or pins or combs made from similar materials comprising beads or flat surfaces or beads placed into pits in flat surfaces such as wafers (e.g., silicon wafers). Examples of solid supports also include acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/9, nylon 6/10, nylon 6/12, nylon 11 and nylon 12), polycarylonitrile (PAN), polyacrylate, polycarbonate, polybutylene terephthalate (PBT), polyethylene terephthalate (PET), polyethylene (including low density, linear low density, high density, cross-linked and ultra-high molecular weight grades), polypropylene homopolymer, polypropylene copolymers, polystyrene (including general purpose and high impact grades), polytetrafluoroethylene (PTFE), fluorinated ethylene-propylene (FEP), ethylene-tetrafluoroethylene (ETFE), perfluoroalkoxyethylene (PFA), polyvinyl fluoride (PVA), polyvinylidene fluoride (PVDF), polychlorotrifluoroethylene (PCTFE), polyethylene-chlorotrifluoroethylene (ECTFE), polyvinyl alcohol (PVA), silicon styrene-acrylonitrile (SAN), styrene maleic anhydride (SMA), metal oxides, and glass.

The biarsenical molecule may be contacted with a bonding partner in a living cell. The bonding partner may be introduced into a cell or produced within a cell. A biarsenical molecule capable of traversing a biological membrane is preferable when the biarsenical molecule is introduced outside the cell and the bonding partner is inside the cell. Typically, a membrane traversing biarsenical molecule is preferable for use within a living cell. Examples of uses of the biarsenical molecule/target sequence complex within cells include polypeptide interactions, polypeptide location, polypeptide quantifications, nucleic acid molecule identification and location.

When in vivo labeling of cells is employed, it will often be advantageous to add one or more compounds to the cell solution which absorb background light. One example of such a compound is Disperse Blue 3. Methods involving the use of such compounds are disclosed in U.S. Pat. Nos. 6,200,762, 6,214,563, and 6,221,612, the entire disclosures of which are incorporated herein by reference.

The biarsenical molecule may be used to induce a more favorable conformation of the bonding partner. For example, the bonding partner may have two possible conformations, but one of the conformations may be more functionally important. The bonding partner when it reacts with the biarsenical molecule may adopt the more functionally important conformation. A functionally important conformation may be, for example, a conformation that can bind a drug.

A tetraarsenical molecule of the present invention can be used to cross-link two bonding partners. Each of the bonding partners includes a target sequence. In a preferred embodiment, each bonding partner contains a target sequence and a carrier molecule. The carrier molecule may be a polypeptide. The polypeptides in each of the bonding partners may be the same. Alternatively, the polypeptides in each bonding partner may be different. The target sequences may be the same or they may be different in each bonding partner. For example, cross-linking of polypeptides may be valuable in studying the effects of polypeptide dimerization on signal transduction. Ho S. N., Biggar S. R., Spencer D. M., Schreiber S. L., and Crabtree G. R., Nature 382: 822-826 (1996); Spencer D. M., Wandless T. J., Schreiber S. L., and Crabtree G. R. Science 262: 1019-1024 (1993). The carrier polypeptide may be an enzyme or an antibody.

In some embodiments, a bonding partner containing the target sequence and an antibody as the carrier polypeptide may be cross-linked via a tetraarsenical molecule to a bonding partner containing the target sequence and an enzyme, as the carrier polypeptide. Such a composition may be useful, for example, in enzyme immunoassays.

A wide variety of assays exist that use detectable signals as a means to determine the presence or concentration of a particular molecule. Examples of such assays include immunoassays to detect antibodies or antigens, enzyme assays, chemical assays and nucleic acid assays. An above described biarsenical molecule/target sequence complex can be useful in these assays.

In general, assays may be performed as follows. A sample containing a molecule of interest associated with either the biarsenical molecule or the target sequence may be contacted with the target sequence or the biarsenical molecule, respectively. The resulting solution is then monitored for the presence of a detectable signal or a change in a detectable signal.

A particularly useful characteristic of the biarsenical molecule/target sequence complex is that the complex may be dissociated by adding an excess reagent such as EDT. The dissociation of the complex may be particularly useful in assays, polypeptide purification schemes, and within cells.

The invention will be further understood with reference to the following examples, which are purely exemplary, and should not be taken as limiting the true scope of the present invention as described in the claims.

The invention further includes nucleic acid molecules which encode target sequences, as well as other peptides and/or proteins of the invention. These nucleic acid molecules may vary in sequence based upon the codons chosen to encode individual amino acids. Codons vary, to some extent, with the translation system of the organism used but one example of a codon usage chart is set out below in Table 1. Codon selection is one example of a way that nucleic acids of the invention may be designed to have one or more desired properties. One example of a desired property is efficiency of expression in a particular cell type. As one skilled in the art would recognize, particular cells often have prefer particular codons which are used for certain amino acids.

TABLE 1

Codon usage Chart

| TTT | F | Phe | TCT | S | Ser | TAT | Y | Tyr | TGT | C | Cys |
|---|---|---|---|---|---|---|---|---|---|---|---|
| TTC | F | Phe | TCC | S | Ser | TAC | Y | Tyr | TGC | C | Cys |
| TTA | L | Leu | TCA | S | Ser | TAA | * | Ter | TGA | * | Ter |
| TTG | L | Leu | TCG | S | Ser | TAG | * | Ter | TGG | W | Trp |
| CTT | L | Leu | CCT | P | Pro | CAT | H | His | CGT | R | Arg |
| CTC | L | Leu | CCC | P | Pro | CAC | H | His | CGC | R | Arg |
| CTA | L | Leu | CCA | P | Pro | CAA | Q | Gln | CGA | R | Arg |
| CTG | L | Leu | CCG | P | Pro | CAG | Q | Gln | CGG | R | Arg |
| ATT | I | Ile | ACT | T | Thr | AAT | N | Asn | AGT | S | Ser |
| ATC | I | Ile | ACC | T | Thr | AAC | N | Asn | AGC | S | Ser |
| ATA | I | Ile | ACA | T | Thr | AAA | K | Lys | AGA | R | Arg |

TABLE 1-continued

Codon usage Chart

| ATG | M | Met | ACG | T | Thr | AAG | K | Lys | AGG | R | Arg |
|---|---|---|---|---|---|---|---|---|---|---|---|
| GTT | V | Val | GCT | A | Ala | GAT | D | Asp | GGT | G | Gly |
| GTC | V | Val | GCC | A | Ala | GAC | D | Asp | GGC | G | Gly |
| GTA | V | Val | GCA | A | Ala | GAA | E | Glu | GGA | G | Gly |
| GTG | V | Val | GCG | A | Ala | GAG | E | Glu | GGG | G | Gly |

For each triplet, the single and three letter abbreviation for the encoded amino acid is shown. Stop codons are represented by *.

The invention also includes nucleic acid molecules that encode fusion proteins comprising the following three polypeptide portions: (1) a polypeptide encoded by a nucleic acid of interest (e.g., a nucleic acid segment which has been inserted into a vector), (2) a peptide or polypeptide encoded by all or part of cloning site (e.g., a restriction enzyme recognition site, a recombination site, a topoisomerase recognition site, etc.), and (3) a target sequence. The invention further includes fusion proteins which are encoded by such nucleic acid molecules, as well as (a) methods for making such nucleic acid molecules and fusions proteins and (b) compositions (e.g., reaction mixtures) comprising such nucleic acid molecules and fusions proteins.

The polypeptide portions referred to above may be connected in any order to form fusion proteins of the invention but typical orders included (1)-(2)-(3) and (3)-(2)-(1). In particular instances, a peptide or polypeptide encoded by all or part of cloning site may comprise one to three, three to five, five to eight, eight to ten, ten to fifteen, or fourteen to twenty amino acids.

Cloning sites particularly suited for use with target sequences of the invention are topoisomerase recognition sites and GATEWAY™ recombination sites. These sites, as well as methods for using such sites, have previously been described in U.S. patent application Ser. No. 10/005,876, filed Dec. 7, 2001, U.S. patent application Ser. No. 10/792, 035, filed Mar. 4, 2004 and U.S. Application No. 60/487,301, filed Jul. 16, 2003, and PCT Publication WO 02/46372, the entire disclosures of which are incorporated herein by reference.

As noted above, one component of fusion proteins of the invention may be encoded by a cloning site, such as a topoisomerase recognition site. Exemplary topoisomerase recognition sites comprise the sequences CCCTT and TCCTT. Topoisomerase recognition sequences are typically five nucleotides in length. Depending upon the reading frame of the polypeptides on either side of the topoisomerase site, it may be desirable to add one or two nucleotides on either side of the site and introduce either a di- or tri-peptide into the final fusion protein. For example, one nucleotide may be added at either end of the topoisomerase site, for example, so that the site with the additional nucleotide encodes a di-peptide. For the topoisomerase recognition sequence CCCTT, the codon duplexes thus generated are ACC CTT (encoding Thr-Leu), GCC CTT, (encoding Ala-Leu), TCC CTT, (encoding Ser-Leu), CCC CTT, (encoding Pro-Leu), CCC TTA, (encoding Pro-Leu), CCC TTG, (encoding Pro-Leu), CCC TTT, (encoding Pro-Phe), and CCC TTC, (encoding Pro-Phe). In many organisms, the dipeptides encoded by these codon duplexes would be Thr-Leu, Ser-Leu, Pro-Leu, Ala-Leu, Pro-Leu, and Pro-Phe. Thus, fusion proteins of the invention include those which comprise the following polypeptide portions: (1)-Thr-Leu-(3), (3)-Thr-Leu-(1), (1)-Ser-Leu-(3), (3)-Ser-Leu-(1), (1)-Pro-Leu-(3), (3)-Pro-Leu-(1), (1)-Ala-Leu-(3), (3)-Ala-Leu-(1), (1)-Pro-Leu-(3), (3)-Pro-Leu-(1), (1)-Pro-Phe-(3), and (3)-Pro-Phe-(1).

In some embodiments, it may be desirable to add two nucleotides on either side of a topoisomerase site so as to bring polypeptides encoded on the nucleic acid molecules to be joined into the same reading frame. This may result in the addition of a tri-peptide to the final fusion protein. For example, if the polypeptide encoded by the nucleic acid molecule on one side of the topoisomerase site is in the first reading frame and the polypeptide encoded by the nucleic acid molecule on the other side of the topoisomerase site is in the third reading frame, it may be desirable to add two nucleotides to either side of the topoisomerase site (or equivalently to either nucleic acid molecule) to bring the polypeptides into the same reading frame. For example, in the sequence ATG-CCCTT-XXATG (SEQ. ID NO: 51), the first ATG represents a polypeptide in the first reading frame of a first nucleic acid molecule CCCTT represents the nucleotides of the topoisomerase site and XXATG represents the nucleic acid sequence encoding a polypeptide in the third reading frame on the second nucleic acid molecule. In order to bring the two polypeptides into the same reading frame (i.e., put the ATG codons in the same reading frame) two nucleotides must be added to either side of the topoisomerase site or one to each side. When two nucleotides are added, for example, on the 3' side of the topoisomerase site, the nucleic acid sequence and first two amino acids would be as above (i.e., CCC TTA, (encoding Pro-Leu), CCC TTG, (encoding Pro-Leu), CCC TTT, (encoding Pro-Phe), and CCC TTC, (encoding Pro-Phe) and the third amino acid could be any of the twenty naturally occurring amino acids depending upon the nucleotides one the second nucleic acid molecule (i.e., XX) and the second of the two nucleotides added. If the two nucleotides added are $N_1$ and $N_2$ the final nucleic acid molecule would have the sequence ATG-CCC-TTN$_1$-N$_2$XX-ATG (SEQ. ID NO: 52). Thus, the tri-peptide may have the sequence Pro-(Phe or Leu)-Xaa where Xaa represents any of the naturally occurring amino acids. In like fashion, one skilled in the art can readily determine the peptide sequences generated by adding two nucleotides to the 5'-side of the topoisomerase site, or by adding one nucleotide to either side of the topoisomerase site. Fusion proteins comprising such sequences are within the scope of the present invention.

One example of an amino acid sequence which may be encoded by a cloning site is the following: Pro-Ala-Phe-Leu-Tyr-Lys-Val-Gly-Ile-Ile-Arg-Lys-His-Cys-Leu-Ser-Ile-Cys-Cys-Asn-Glu-Gln-Val-Thr-Ile-Ser-Gln-Asn-Lys-Ile-Ile-Ile (SEQ ID NO: 48). This amino acid sequence is encoded by one of the six reading frames of an attL2 recombination site. This amino acid sequence may be present in fusion proteins due to the fact that there are no stop codons present in the reading of the attL2 site which encodes this amino acid sequence. Thus, when a fusion protein of the order (1)-(2)-(3) or (3)-(2)-(1) contains an attL2 site as the cloning site (i.e., component (2)). The amino acid sequence referred to above will often be encoded by an attL2 recombination site. Further this amino acid sequence may only comprise part of the amino acid sequence encoded by a portion of an attL2 recombination site. Thus, in particular embodiments, proteins of the invention will contain at least two, three, four, five, six, seven, eight, nine, ten, eleven, twelve, thirteen, fourteen, fifteen, sixteen, seventeen, eighteen, nineteen, twenty, twenty-five, or thirty amino acids of the sequence Pro-Ala-Phe-Leu-Tyr-Lys-Val-Gly-Ile-Ile-Arg-Lys-His-Cys-Leu-Ser-Ile-Cys-Cys-Asn-Glu-Gln-Val-Thr-Ile-Ser-Gln-Asn-Lys-Ile-Ile-Ile (SEQ ID NO: 49). The invention further includes fusion proteins which contain a full-length amino acid sequence encoded by any of the six reading frames of any of the recombination sites set out in Table 2, as well as sub-portions of such amino acid sequences of the lengths set out above for the attL2 recombination site.

TABLE 4

Nucleotide sequences of att sites.

| Name | Sequence | SEQ ID NO |
|---|---|---|
| AttB0 | AGCCTGCTTT TTTATACTAA CTTGAGC | (SEQ. ID NO: 12) |
| AttP0 | GTTCAGCTTT TTTATACTAA GTTGGCA | (SEQ. ID NO: 13) |
| AttL0 | AGCCTGCTTT TTTATACTAA GTTGGCA | (SEQ. ID NO: 14) |
| AttR0 | GTTCAGCTTT TTTATACTAA CTTGAGC | (SEQ. ID NO: 15) |
| AttB1 | AGCCTGCTTT TTTGTACAAA CTTGT | (SEQ. ID NO: 16) |
| AttP1 | GTTCAGCTTT TTTGTACAAA GTTGGCA | (SEQ. ID NO: 17) |
| AttL1 | AGCCTGCTTT TTTGTACAAA GTTGGCA | (SEQ. ID NO: 18) |
| AttR1 | GTTCAGCTTT TTTGTACAAA CTTGT | (SEQ. ID NO: 19) |
| AttB2 | ACCCAGCTTT CTTGTACAAA GTGGT | (SEQ. ID NO: 20) |
| AttP2 | GTTCAGCTTT CTTGTACAAA GTTGGCA | (SEQ. ID NO: 21) |
| AttL2 | ACCCAGCTTT CTTGTACAAA GTTGGCA | (SEQ. ID NO: 22) |
| AttR2 | GTTCAGCTTT CTTGTACAAA GTGGT | (SEQ. ID NO: 23) |
| AttB5 | CAACTTTATT ATACAAAGTT GT | (SEQ. ID NO: 24) |
| AttP5 | GTTCAACTTT ATTATACAAA GTTGGCA | (SEQ. ID NO: 25) |
| AttL5 | CAACTTTATT ATACAAAGTT GGCA | (SEQ. ID NO: 26) |
| AttR5 | GTTCAACTTT ATTATACAAA GTTGT | (SEQ. ID NO: 27) |
| AttB11 | CAACTTTTCT ATACAAAGTT GT | (SEQ. ID NO: 28) |
| AttP11 | GTTCAACTTT TCTATACAAA GTTGGCA | (SEQ. ID NO: 29) |
| AttL11 | CAACTTTTCT ATACAAAGTT GGCA | (SEQ. ID NO: 30) |
| AttR11 | GTTCAACTTT TCTATACAAA GTTGT | (SEQ. ID NO: 31) |
| AttB17 | CAACTTTTGT ATACAAAGTT GT | (SEQ. ID NO: 32) |
| AttP17 | GTTCAACTTT TGTATACAAA GTTGGCA | (SEQ. ID NO: 33) |
| AttL17 | CAACTTTTGT ATACAAAGTT GGCA | (SEQ. ID NO: 34) |
| AttR17 | GTTCAACTTT TGTATACAAA GTTGT | (SEQ. ID NO: 35) |
| AttB19 | CAACTTTTTC GTACAAAGTT GT | (SEQ. ID NO: 36) |
| AttP19 | GTTCAACTTT TTCGTACAAA GTTGGCA | (SEQ. ID NO: 37) |
| AttL19 | CAACTTTTTC GTACAAAGTT GGCA | (SEQ. ID NO: 38) |
| AttR19 | GTTCAACTTT TTCGTACAAA GTTGT | (SEQ. ID NO: 39) |
| AttB20 | CAACTTTTTG GTACAAAGTT GT | (SEQ. ID NO: 40) |

TABLE 4-continued

Nucleotide sequences of att sites.

| | | |
|---|---|---|
| AttP20 | GTTCAACTTT TTGGTACAAA GTTGGCA | (SEQ. ID NO: 41) |
| AttL20 | CAACTTTTTG GTACAAAGTT GGCA | (SEQ. ID NO: 42) |
| AttR20 | GTTCAACTTT TTGGTACAAA GTTGT | (SEQ. ID NO: 43) |
| AttB21 | CAACTTTTTA ATACAAAGTT GT | (SEQ. ID NO: 44) |
| AttP21 | GTTCAACTTT TTAATACAAA GTTGGCA | (SEQ. ID NO: 45) |
| AttL21 | CAACTTTTTA ATACAAAGTT GGCA | (SEQ. ID NO: 46) |
| AttR21 | GTTCAACTTT TTAATACAAA GTTGT | (SEQ. ID NO: 47) |

EXAMPLES

Example 1

Target Sequence Generated on AcpS

A target sequence that includes the SlyD (SEQ. ID NO: 4) tetracysteine sequence, CCGGKGNGGCGC (SEQ. ID NO: 5) was introduced onto the Carboxy-terminus of Acyl Carrier Protein S (AcpS). Since AcpS has only one endogenous cysteine amino acid and since AcpS is a robust stable protein, a substitution at the Carboxy-terminus could be made without altering the solubility of the properly folded protein. The four cysteines comprising the SlyD tetracysteine sequence were introduced at the carboxy-terminus of the protein as seen in SEQ. ID NO: 6. The mutated AcpS is referred to as AcpS+ 4Cys. The substitutions were generated using polymerase chain reaction with primers specific for the encoding the expression of the desired tetracysteine sequence. The nucleic acid sequence encoding the cysteine substituted AcpS was inserted into the pRSET vector (Invitrogen, Carlsbad, Calif., Catalog #V351-20) using restriction sites inherent to the vector's multiple cloning site. After amplification in DH5 bacteria, the vector was expressed using in vitro transcription and translation. See also, U.S. Provisional Patent Application No. 60/614,590, filed Oct. 1, 2004 and U.S. patent application Ser. No. 10/954,951, filed Oct. 1, 2004, incorporated by reference herein in their entireties, disclosing additional compositions and methods for in vitro transcription and translation.

Figure 14:
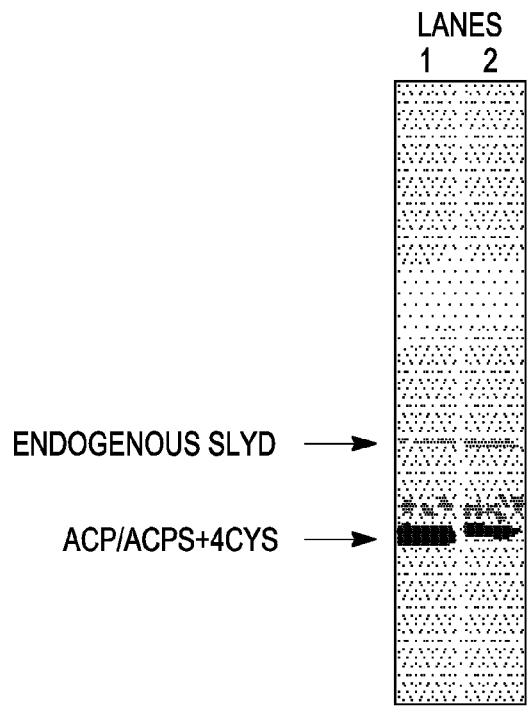
FIG. 14 shows biarsenical (FlAsH-EDT$_2$) labeling of the SlyD tetracysteine sequence heterologously expressed on AcpS and FlAsH-EDT$_2$ labeling of ACP-CCPGCC (SEQ. ID NO: 53). Cell extracts from in vitro protein synthesis reactions were labeled with FlAsH-EDT$_2$ and separated by SDS-PAGE. Lane 1 is ACP-CCPGCC (SEQ. ID NO: 53) and Lane 2 contains AcpS+4Cys.

In vitro protein synthesis was carried out using the Expressway™ in vitro protein synthesis kit (Invitrogen, Carlsbad, Calif., Catalog #K9600-02). Following the manufacture's protocol 1 μg of AcpS vector DNA was added to a total volume of 50 μL of S30 E. coli extract and reaction buffer. As a control, a tetracysteine (CCPGCC) (SEQ. ID NO: 53) version of Acyl Carrier protein (ACP) (SEQ. ID NO: 7) was also expressed via the Expressway™ kit. The reaction was placed at 37° C. with 225 rpm shaking for two hours. After incubation 5 μL of RNase A was added to the reaction, after which an additional 15 minute incubation at 37° C. was performed. Protein from the in vitro protein synthesis reaction was prepared for SDS-PAGE analysis through an acetone precipitation procedure. 5 μl of reaction was added to 20 μL of 100% acetone. After mixing well the acetone solution was centrifuged for 5 minutes at room temperature in a microcentrifuge at 12,000 rpm. The supernatant was removed and the pellet was allowed to dry for 5 minutes. The pellet was resuspended in a 50 μL volume of LDS sample buffer (Invitrogen, Carlsbad, Calif., Catalog #NP0007) containing 10 μM FlAsH-EDT$_2$. The samples were heated to 70° C. for 10 minutes and 10 μL of the samples were then loaded onto a 4-12% NUPAGE® pre-cast gel (Invitrogen, Carlsbad, Calif.) using MES running buffer. The gel was electrophoresed at 200 volts for about 30 minutes. Immediately following electrophoresis the gel was removed from the cassette and visualized on a UV light box. FIG. 14 shows equivalent labeling between the CCGGKGNGGCGC (SEQ. ID NO: 5) and CCPGCC (SEQ. ID NO: 53) sequences. This experiment demonstrated the feasibility of using FlAsH-EDT$_2$ to label a protein containing the SlyD tetracysteine sequence and yield results comparable to the standard tetracysteine sequence. See also, U.S. Provisional patent application Ser. No. 10/971, 606, filed Oct. 22, 2004, "Compositions, Methods and Kits for Biarsenical Fluorophore Labeling," naming as inventors: Roumen A. Bogoev, Joseph W. Amshey and George Hanson, incorporated by reference herein in its entirety, for additional disclosure of compositions and methods for labeling and detection of biarsenical molecules.

Example 2

Binding Modes for Biarsenical Molecules to Target Sequences

Figure 15:
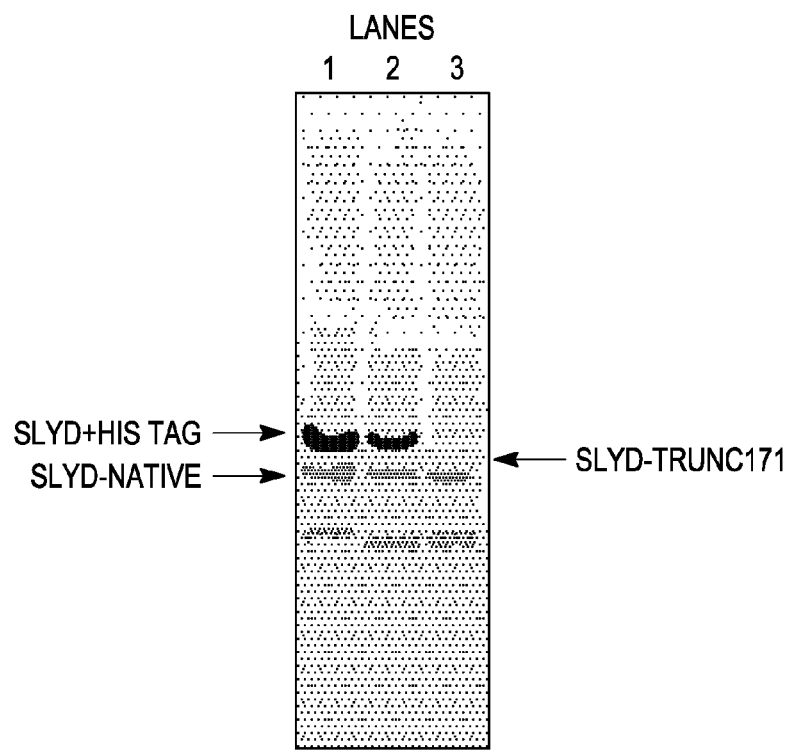
FIG. 15 shows biarsenical (FlAsH-EDT$_2$) labeling of several versions of SlyD. Cell extracts from in vitro protein synthesis reactions were labeled with FlAsH-EDT$_2$ and separated by SDS-PAGE. Lane 1 is full length, hexahistidine tagged SlyD (SlyD+His tag), Lane 2 is full length, hexahistidine tagged SlyD with two point mutations: C167A and C168A (SlyD-C167A/C168A), and Lane 5 contains a hexahistidine tagged version of SlyD truncated after position 171 (SlyD-trunc171).

The mode of binding of a biarsenical to a target sequence was examined using the Expressway™ in vitro protein synthesis kit (Invitrogen, Carlsbad, Calif.) and SDS-PAGE. Following the manufacture's protocol 1 μg of SlyD+His tag (SEQ. ID NO: 8), SlyD-C167A/C168A (SEQ. ID NO: 9), and SlyD-trunc171 (SEQ. ID NO: 10) vector DNAs were added to a total volume of 50 μL of S30 E. coli extract and reaction buffer. The reaction was placed at 37° C. with 225 rpm shaking for two hours. After incubation 5 μL of RNase A was added to the reaction, after which an additional 15 minute incubation at 37° C. was performed. Protein from the in vitro protein synthesis reaction was prepared for SDS-PAGE analysis through an acetone precipitation procedure. 5 μl of reaction was added to 20 μL of 100% acetone. After mixing well the acetone solution was centrifuged for 5 minutes at room temperature in a microcentrifuge at 12,000 rpm. The supernatant was removed and the pellet was allowed to dry for 5 minutes. The pellet was resuspended in a 50 μL volume of LDS sample buffer (Invitrogen, Carlsbad, Calif.) containing 10 μM FlAsH-EDT$_2$. The samples were heated to 70° C. for 10 minutes and 10 μL of the samples were then loaded onto a 4-12% NuPAGE® pre-cast gel (Invitrogen, Carlsbad, Calif., Catalog #NP0239 Box) using MES running buffer. The gel was electrophoresed at 200 volts for about 30 minutes. Immediately following electrophoresis the gel was removed from the cassette and visualized on a UV light box. FIG. 15 reveals that identical labeling is observed between SlyD+His tag and SlyD-C167A/C168 and in addition only two cysteines are required for biarsenical labeling.

Figure 16:
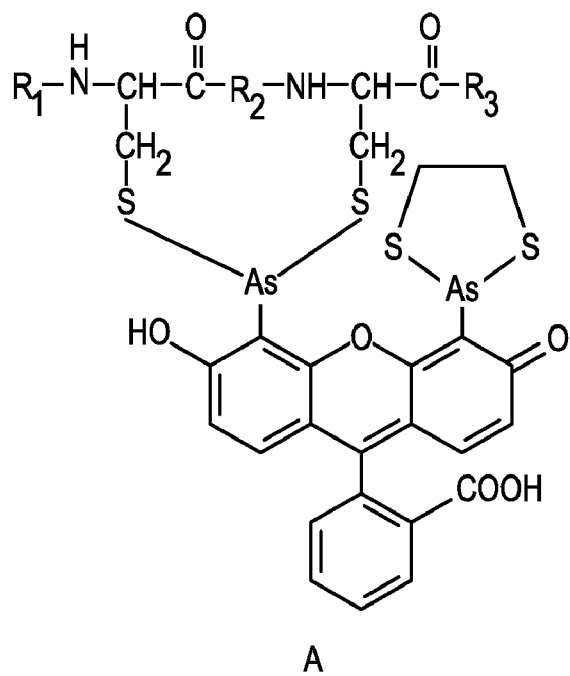
FIG. 16 is a schematic diagram showing the binding of a biarsenical molecule to a polypeptide containing cysteine amino acids. A) Binding of a biarsenical through a single arsenic to a pair of thiols. B) Binding of a biarsenical to a tetracysteine sequence through two arsenics binding to four thiols. In the diagram $R_1$ and $R_3$ can be a polypeptide of any length from zero to 10,000 amino acids and consisting of any combination of amino acids. $R_2$ is a polypeptide of length from zero to eight amino acids and consisting of any combination of amino acids. $R_4$ is any polypeptide of length from zero to 20 amino acids and consisting of any combination of amino acids.
Figure 16:
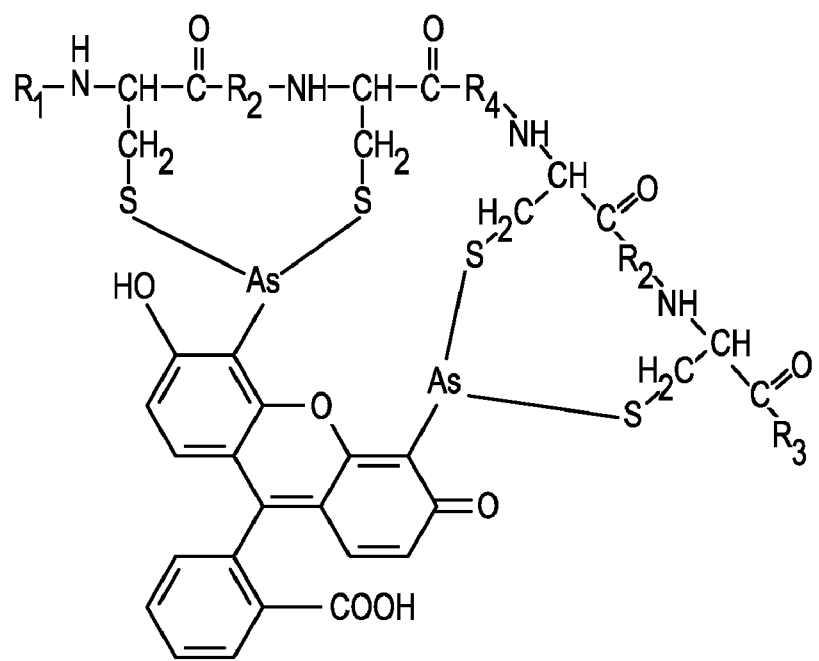

Since labeling of a protein containing either two or four cysteines with a biarsenical is observed, then two modes of binding are possible. In the case of a biarsenical labeling a two cysteine containing protein only a single arsenic is likely involved in binding (FIG. 16A). When four cysteines are present then both arsenics of the biarsenical are able to interact with the four thiol side chains of the cysteine amino acids (FIG. 16B). From the diagram, cysteine amino acids are displaced and 'R' groups are as follows: 1) $R_1$ and $R_3$ can be a polypeptide of any length from zero to 10,000 amino acids and consisting of any combination of amino acids. 2) $R_2$ is a polypeptide of length from zero to eight amino acids and consisting of any combination of amino acids. 3) $R_4$ is any polypeptide of length from zero to 20 amino acids and consisting of any combination of amino acids. This experiment demonstrated the feasibility of using biarsenical molecules to label a protein containing the SlyD tetracysteine comprised of four cysteines or a protein containing only a vicinal pair of cysteines.

Example 3

Specificity of Biarsenical Molecules for Tetracysteine Sequences

To demonstrate specificity of biarsenical compounds for different tetracysteine sequences several chimeric proteins were constructed. The native SlyD sequence (SEQ. ID NO: 4) was cloned into the pRSET vector (Invitrogen, Carlsbad, Calif.) using standard molecular biology techniques. Purified protein was produced from this vector by first transforming BL21 (DE3) cells (Invitrogen, Carlsbad, Calif., Catalog #C6010-03) and plated on LB-ampicillin plates. A single colony was selected and grown in one liter of liquid LB broth to a density of 1 O.D. and 1 mM IPTG was added to induce protein expression. After three hours of protein induction the culture was harvested by centrifugation at 10,000×g for 5 minutes at 4° C. The cell pellet was resuspended in 50 mM HEPES (pH 7.5), 140 mM NaCl and sonicated on ice for a total of two minutes. The *E. coli* lysate was separated by centrifugation at 25,000×g for 20 minutes at 4° C. The supernatant contained the soluble protein and consequently it was loaded onto a $Ni^{2+}$-NTA column equilibrated in 50 mM HEPES (pH 7.5), 140 mM NaCl buffer. The column was washed with three column volumes of 50 mM HEPES (pH 7.5), 140 mM NaCl and non-specific binding proteins were removed by washing with 50 mM HEPES (pH 7.5), 140 mM NaCl, and 20 mM Imidazole. To elute the desired hexahistidine tagged SlyD, a solution of 50 mM HEPES (pH 7.5), 140 mM NaCl, and 250 mM Imidazole was added to the column. The protein eluted at greater than 90% purity.

ACP (Invitrogen, Madison, Wis., Catalog #P3080) was mixed at approximately 2:1 molar ratio with SlyD-His tag. The proteins were put in SDS-PAGE sample buffer supplemented with 10 μM FlAsH-$EDT_2$, Cy3-$EDT_2$, or Cy5-$EDT_2$ and electrophoresed at 150 volts on a 4-20% Tris-glycine pre-cast Novex gel (Invitrogen, Carlsbad, Calif.). Immediately following electrophoresis the gel was imaged on a Fuji Film FLA 5000 laser gel scanner. FIG. 17 reveals that FlAsH-$EDT_2$ binds to both SlyD+His tag and ACP, whereas Cy3-$EDT_2$ and Cy5-$EDT_2$ only label ACP. Therefore, the SlyD tetracysteine sequence (SEQ. ID NO: 5) uniquely binds to biarsenical molecules and not to bis-arsenicals. This experiment demonstrated the feasibility of specificity of bi/bis-arsenical labeling of tetracysteine sequences.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

Although the invention has been described with reference to the above examples, it will be understood that modifications and variations are encompassed within the spirit and scope of the invention. Accordingly, the invention is limited only by the following claims.

What is claimed is:

1. A method of labeling a carrier molecule, comprising:
   a) providing a bonding partner comprising the carrier molecule and a target sequence, and
   b) contacting the bonding partner with a biarsenical molecule under conditions wherein the biarsenical molecule reacts with the target sequence, wherein the target sequence comprises Cys-Cys-$X_1$-$X_1$-$X_2$-$X_1$-$X_3$-$X_1$-$X_1$-Cys-$X_1$-Cys-$X_2$ (SEQ. ID NO: 3), wherein:

$X_1$ is an amino acid having a non-polar side chain,
   $X_2$ is an amino acid having a basic side chain, and
   $X_3$ is an amino acid having a non-ionic polar side chain, and wherein the biarsenical molecule has the formula:

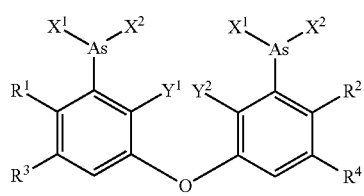

and tautomers, anhydrides, and salts thereof;

wherein:

each $X^1$ or $X^2$ is independently Cl, Br, I, $OR^a$, or $SR^a$, or $X^1$ and $X^2$ together with the arsenic atom form a ring having the formula:

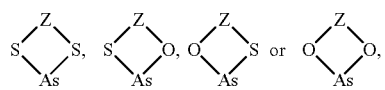

$R^a$ is H, $C_1$-$C_4$ alkyl, $CH_2CH_2OH$, $CH_2COOH$, or CN;

Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;

$Y^1$ and $Y^2$ are each independently H or $CH_3$, or $Y^1$ and $Y^2$ together form a ring such that the biarsenical molecule has the formula

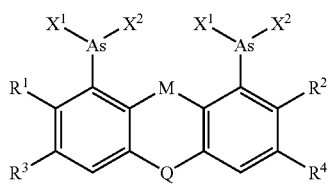

wherein:
M is O, S, $CH_2$, $C(CH_3)_2$, or NH;
$R^1$ and $R^2$ are each independently $OR^a$, OAc, $NR^aR^b$, or H;
$R^3$ and $R^4$ are each independently H, F, Cl, Br, I, $OR^a$, or $R^a$; or
$R^1$ together with $R^3$, or $R^2$ together with $R^4$, or both, form a ring in which
(i) one of $R^1$ or $R^3$ is $C_2$-$C_3$ alkyl and the other is $NR^a$ and
(ii) one of $R^2$ and $R^4$ is $C_2$-$C_3$ alkyl and the other is $NR^a$;
$R^b$ is H, $C_1$-$C_4$ alkyl, $CH_2CH_2OH$, $CH_2COOH$, or CN;
Q is $CR^aR^b$, $CR^aOR^b$, C=O, or a spirolactone having the formula:

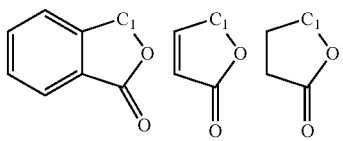

wherein the Spiro linkage is formed at $C_1$.

2. The method of claim 1, wherein the biarsenical molecule generates a detectable signal.

3. The method of claim 2, further comprising monitoring the detectable signal.

4. The method of claim 2, wherein the signal is a fluorescent signal.

5. The method of claim 1, wherein the biarsenical molecule is coupled to a solid phase.

6. The method of claim 1, wherein the target sequence is coupled to a solid phase.

7. The method of claim 1, wherein the carrier molecule is a polypeptide.

8. The method of claim 7, wherein the polypeptide is an antibody or an enzyme.

9. The method of claim 1, wherein $X_1$ is glycine, alanine, valine, leucine, isoleucine, methionine, proline, phenylalanine, or tryptophan.

10. The method of claim 1, wherein $X_2$ is lysine, arginine, or histidine.

11. The method of claim 1, wherein $X_3$ is asparagine, glutamine, serine, or threonine.

12. The method of claim 1, wherein the target sequence is Cys-Cys-gly-gly-lys-gly-asn-gly-gly-Cys-gly-Cys-his (SEQ. ID NO: 50).

13. A method of purifying a bonding partner, comprising:
a) providing a bonding partner comprising a target sequence wherein the target sequence comprises Cys-Cys-$X_1$-$X_1$-$X_1$-$X_1$-$X_3$-$X_1$-$X_1$-Cys-$X_1$-Cys-$X_2$ (SEQ. ID NO: 3), wherein:
$X_1$ is an amino acid having a non-polar side chain,
$X_2$ is an amino acid having a basic side chain, and
$X_3$ is an amino acid having a non-ionic polar side chain, and wherein the target sequence reacts with a biarsenical molecule having the structure:

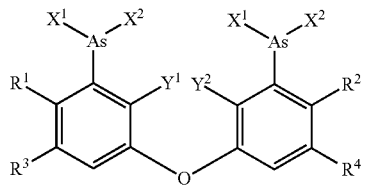

and tautomers, anhydrides, and salts thereof;
wherein:
each $X^1$ or $X^2$ is independently Cl, Br, I, $OR^a$, or $SR^a$, or $X^1$ and $X^2$ together with the arsenic atom form a ring having the formula:

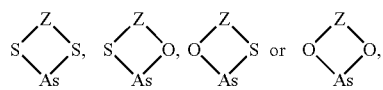

$R^a$ is H, $C_1$-$C_4$ alkyl, $CH_2CH_2OH$, $CH_2COOH$, or CN;
Z is 1,2-ethanediyl, 1,2-propanediyl, 2,3-butanediyl, 1,3-propanediyl,
1,2 benzenediyl, 4-methyl-1,2-benzenediyl, 1,2-cyclopentanediyl,
1,2-cyclohexanediyl, 3-hydroxy-1,2-propanediyl, 3-sulfo-1,2-propanediyl, or
1,2-bis(carboxy)-1,2-ethanediyl;
$Y^1$ and $Y^2$ are each independently H or $CH_3$, or
$Y^1$ and $Y^2$ together form a ring such that the biarsenical molecule has the formula

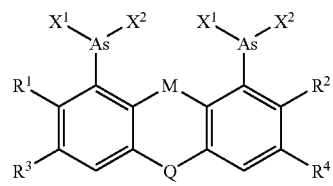

wherein:
M is O, S, $CH_2$, $C(CH_3)_2$, or NH;
$R^1$ and $R^2$ are each independently $OR^a$, OAc, $NR^aR^b$, or H;
$R^3$ and $R^4$ are each independently H, F, Cl, Br, I, $OR^a$, or $R^a$; or
$R^1$ together with $R^3$, or $R^2$ together with $R^4$, or both, form a ring in which
(i) one of $R^1$ or $R^3$ is $C_2$-$C_3$ alkyl and the other is $NR^a$ and
(ii) one of $R^2$ and $R^4$ is $C_2$-$C_3$ alkyl and the other is $NR^a$;
$R^b$ is H, $C_1$-$C_4$ alkyl, $CH_2CH_2OH$, $CH_2COOH$, or CN;
Q is $CR^aR^b$, $CR^aOR^b$, C=O, or a spirolactone having the formula:

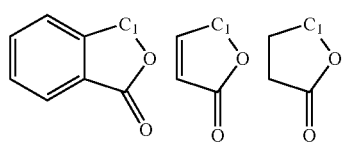

wherein the Spiro linkage is formed at $C_1$;
b) contacting the bonding partner with the biarsenical molecule, wherein the biarsenical molecule is coupled to a solid phase, and
c) eluting the bonding partner from the biarsenical molecule by contacting the biarsenical molecule with a dithiol.

14. The method of claim 13, wherein the carrier molecule is a protein.

15. The method of claim 14, wherein the protein is an antibody or an enzyme.

16. The method of claim 13, wherein the biarsenical compound is membrane permeable.

17. The method of claim 13, wherein the dithiol is selected from the group consisting of 1,2-benzendithiol, 1,2-cyclohexanedithiol and 1,2-ethanedithiol.

18. The method of claim 13, wherein $X_1$ of SEQ ID NO: 3 is glycine, alanine, valine, leucine, isoleucine, methionine, proline, phenylalanine, or tryptophan.

19. The method of claim 13, wherein $X_2$ of SEQ ID NO:3 is lysine, arginine, or histidine.

20. The method of claim 13, wherein $X_3$ of SEQ ID NO:3 is asparagine, glutamine, serine, or threonine.

21. The method of claim 13, wherein the target sequence is Cys-Cys-Gly-Gly-Lys-Gly-Asn-Gly-Gly-Cys-Gly-Cys-His (SEQ. ID. NO: 50).

22. The method of claim 13, wherein the biarsenical molecule has the following structure:

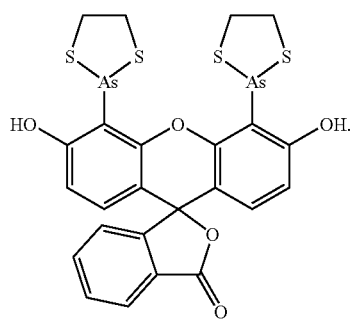

23. The method of claim 1, wherein the biarsenical molecule has the following structure:

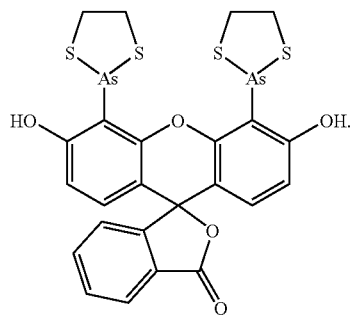

* * * * *

UNITED STATES PATENT AND TRADEMARK OFFICE
CERTIFICATE OF CORRECTION

| | | |
|---|---|---|
| PATENT NO. | : 8,133,709 B2 | |
| APPLICATION NO. | : 12/062031 | |
| DATED | : March 13, 2012 | |
| INVENTOR(S) | : George Hanson | |

It is certified that error appears in the above-identified patent and that said Letters Patent is hereby corrected as shown below:

Claim 1, column 57, lines 58-65, that portion of the formula reading "O" should read --Q--.

Claim 13, column 59, line 62, "Cys-X1-X1-X1-X1-X3-X1-X1-Cys-X1-Cys-X2" should read --Cys-X1-X1-X2-X1-X3-X1-X1-Cys-X1-Cys-X2--;

Claim 13, column 60, lines 5-10, that portion of the formula reading "O" should read --Q--.

Signed and Sealed this
Eleventh Day of September, 2012

David J. Kappos
*Director of the United States Patent and Trademark Office*

SEQUENCE LISTING

```
<160> NUMBER OF SEQ ID NOS: 53

<210> SEQ ID NO 1
<211> LENGTH: 6
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: tetracysteine motif
<220> FEATURE:
<221> NAME/KEY: MISC_FEATURE
<222> LOCATION: (3)..(4)
<223> OTHER INFORMATION: Xaa can be any amino acid except cysteine

<400> SEQUENCE: 1

Cys Cys Xaa Xaa Cys Cys
1               5

<210> SEQ ID NO 2
<211> LENGTH: 13
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: tetracysteine sequence
<220> FEATURE:
<221> NAME/KEY: MISC_FEATURE
<222> LOCATION: (3)..(9)
<223> OTHER INFORMATION: Xaa can be any amino acid
<220> FEATURE:
<221> NAME/KEY: MISC_FEATURE
<222> LOCATION: (11)..(11)
```

```
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid

<400> SEQUENCE: 2

Cys Cys Xaa Xaa Xaa Xaa Xaa Xaa Xaa Cys Xaa Cys Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: tetracysteine sequence
<220> FEATURE:
<221> NAME/KEY: MISC_FEATURE
<222> LOCATION: (3)..(4)
<223> OTHER INFORMATION: Xaa is an amino acid having a non-polar side
      chain
<220> FEATURE:
<221> NAME/KEY: MISC_FEATURE
<222> LOCATION: (5)..(5)
<223> OTHER INFORMATION: Xaa is an amino acid having a basic side chain
<220> FEATURE:
<221> NAME/KEY: MISC_FEATURE
<222> LOCATION: (6)..(6)
<223> OTHER INFORMATION: Xaa is an amino acid having a non-polar side
      chain
<220> FEATURE:
<221> NAME/KEY: MISC_FEATURE
<222> LOCATION: (7)..(7)
<223> OTHER INFORMATION: Xaa is an amino acid having a non-ionic polar
      side chain
<220> FEATURE:
<221> NAME/KEY: MISC_FEATURE
<222> LOCATION: (8)..(9)
<223> OTHER INFORMATION: Xaa is an amino acid having a non-polar side
      chain
<220> FEATURE:
<221> NAME/KEY: MISC_FEATURE
<222> LOCATION: (11)..(11)
<223> OTHER INFORMATION: Xaa is an amino acid having a non-polar side
      chain
<220> FEATURE:
<221> NAME/KEY: MISC_FEATURE
<222> LOCATION: (13)..(13)
<223> OTHER INFORMATION: Xaa is an amino acid having a basic side chain

<400> SEQUENCE: 3

Cys Cys Xaa Xaa Xaa Xaa Xaa Xaa Xaa Cys Xaa Cys Xaa
1               5                   10

<210> SEQ ID NO 4
<211> LENGTH: 196
<212> TYPE: PRT
<213> ORGANISM: Artificial Sequence
<220> FEATURE:
<223> OTHER INFORMATION: Chemically Synthesized

<400> SEQUENCE: 4

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60
```

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
            115                 120                 125

Asn Leu Lys Phe Asn Val Glu Val Ala Ile Arg Glu Ala Thr Glu
130                 135                 140

Glu Glu Leu Ala His Gly His Val His Gly Ala His Asp His His
145                 150                 155                 160

Asp His Asp His Asp Gly Cys Cys Gly His Gly His Asp His Gly
                165                 170                 175

His Glu His Gly Gly Glu Gly Cys Cys Gly Lys Gly Asn Gly Gly
                180                 185                 190

Cys Gly Cys His
            195

<210> SEQ ID NO 5
<211> LENGTH: 12
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: SlyD tetracysteine sequence

<400> SEQUENCE: 5

Cys Cys Gly Gly Lys Gly Asn Gly Gly Cys Gly Cys
1               5                   10

<210> SEQ ID NO 6
<211> LENGTH: 143
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: AcpS

<400> SEQUENCE: 6

Met Ala Ile Leu Gly Leu Gly Thr Asp Ile Val Glu Ile Ala Arg Ile
1               5                   10                  15

Glu Ala Val Ile Ala Arg Ser Gly Asp Arg Leu Ala Arg Arg Val Leu
                20                  25                  30

Ser Asp Asn Glu Trp Ala Ile Trp Lys Thr His His Gln Pro Val Arg
            35                  40                  45

Phe Leu Ala Lys Arg Phe Ala Val Lys Glu Ala Ala Lys Ala Phe
    50                  55                  60

Gly Thr Gly Ile Arg Asn Gly Leu Ala Phe Asn Gln Phe Glu Val Phe
65                  70                  75                  80

Asn Asp Glu Leu Gly Lys Pro Arg Leu Arg Leu Trp Gly Glu Ala Leu
                85                  90                  95

Lys Leu Ala Glu Lys Leu Gly Val Ala Asn Met His Val Thr Leu Ala
            100                 105                 110

Asp Glu Arg His Tyr Ala Cys Ala Thr Val Ile Ile Glu Ser Gly Gly
        115                 120                 125

Glu Gly Cys Cys Gly Gly Lys Gly Asn Gly Gly Cys Gly Cys His

<210> SEQ ID NO 7
<211> LENGTH: 84
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: ACP

<400> SEQUENCE: 7

Met Ser Thr Ile Glu Glu Arg Val Lys Lys Ile Ile Gly Glu Gln Leu
1               5                   10                  15

Gly Val Lys Gln Glu Glu Val Thr Asn Asn Ala Ser Phe Val Glu Asp
                20                  25                  30

Leu Gly Ala Asp Ser Leu Asp Thr Val Glu Leu Val Met Ala Leu Glu
            35                  40                  45

Glu Glu Phe Asp Thr Glu Ile Pro Asp Glu Glu Ala Glu Lys Ile Thr
    50                  55                  60

Thr Val Gln Ala Ala Ile Asp Tyr Ile Asn Gly His Gln Ala Cys Cys
65                  70                  75                  80

Pro Gly Cys Cys

<210> SEQ ID NO 8
<211> LENGTH: 229
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: SlyD plus His tag

<400> SEQUENCE: 8

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Lys Val Ala Lys Asp Leu Val Val Ser Leu Ala Tyr Gln Val
            35                  40                  45

Arg Thr Glu Asp Gly Val Leu Val Asp Glu Ser Pro Val Ser Ala Pro
    50                  55                  60

Leu Asp Tyr Leu His Gly His Gly Ser Leu Ile Ser Gly Leu Glu Thr
65                  70                  75                  80

Ala Leu Glu Gly His Glu Val Gly Asp Lys Phe Asp Val Ala Val Gly
                85                  90                  95

Ala Asn Asp Ala Tyr Gly Gln Tyr Asp Glu Asn Leu Val Gln Arg Val
            100                 105                 110

Pro Lys Asp Val Phe Met Gly Val Asp Glu Leu Gln Val Gly Met Arg
    115                 120                 125

Phe Leu Ala Glu Thr Asp Gln Gly Pro Val Pro Val Glu Ile Thr Ala
130                 135                 140

Val Glu Asp Asp His Val Val Asp Gly Asn His Met Leu Ala Gly
145                 150                 155                 160

Gln Asn Leu Lys Phe Asn Val Glu Val Val Ala Ile Arg Glu Ala Thr
                165                 170                 175

Glu Glu Glu Leu Ala His Gly His Val His Gly Ala His Asp His His
            180                 185                 190

His Asp His Asp His Asp Gly Cys Cys Gly Gly His Gly His Asp His

```
                    195                 200                 205
Gly His Glu His Gly Gly Glu Gly Cys Cys Gly Lys Gly Asn Gly
            210                 215                 220

Gly Cys Gly Cys His
225

<210> SEQ ID NO 9
<211> LENGTH: 229
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: SlyD C167A/C168A

<400> SEQUENCE: 9

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Lys Val Ala Lys Asp Leu Val Val Ser Leu Ala Tyr Gln Val
            35                  40                  45

Arg Thr Glu Asp Gly Val Leu Val Asp Glu Ser Pro Val Ser Ala Pro
        50                  55                  60

Leu Asp Tyr Leu His Gly His Gly Ser Leu Ile Ser Gly Leu Glu Thr
65                  70                  75                  80

Ala Leu Glu Gly His Glu Val Gly Asp Lys Phe Asp Val Ala Val Gly
                85                  90                  95

Ala Asn Asp Ala Tyr Gly Gln Tyr Asp Glu Asn Leu Val Gln Arg Val
            100                 105                 110

Pro Lys Asp Val Phe Met Gly Val Asp Glu Leu Gln Val Gly Met Arg
        115                 120                 125

Phe Leu Ala Glu Thr Asp Gln Gly Pro Val Pro Val Glu Ile Thr Ala
    130                 135                 140

Val Glu Asp Asp His Val Val Val Asp Gly Asn His Met Leu Ala Gly
145                 150                 155                 160

Gln Asn Leu Lys Phe Asn Val Glu Val Val Ala Ile Arg Glu Ala Thr
                165                 170                 175

Glu Glu Glu Leu Ala His Gly His Val His Gly Ala His Asp His His
            180                 185                 190

His Asp His Asp His Asp Gly Ala Ala Gly Gly His Gly His Asp His
        195                 200                 205

Gly His Glu His Gly Gly Glu Gly Cys Cys Gly Lys Gly Asn Gly
            210                 215                 220

Gly Cys Gly Cys His
225

<210> SEQ ID NO 10
<211> LENGTH: 204
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: SlyD trunc171

<400> SEQUENCE: 10

Met Arg Gly Ser His His His His His Gly Met Ala Ser Met Thr
1               5                   10                  15
```

```
Gly Gly Gln Gln Met Gly Arg Asp Leu Tyr Asp Asp Asp Lys Asp
            20                  25                  30

Pro Met Lys Val Ala Lys Asp Leu Val Val Ser Leu Ala Tyr Gln Val
        35                  40                  45

Arg Thr Glu Asp Gly Val Leu Val Asp Glu Ser Pro Val Ser Ala Pro
    50                  55                  60

Leu Asp Tyr Leu His Gly His Gly Ser Leu Ile Ser Gly Leu Glu Thr
65                  70                  75                  80

Ala Leu Glu Gly His Glu Val Gly Asp Lys Phe Asp Val Ala Val Gly
                85                  90                  95

Ala Asn Asp Ala Tyr Gly Gln Tyr Asp Glu Asn Leu Val Gln Arg Val
            100                 105                 110

Pro Lys Asp Val Phe Met Gly Val Asp Glu Leu Gln Val Gly Met Arg
        115                 120                 125

Phe Leu Ala Glu Thr Asp Gln Gly Pro Val Pro Val Glu Ile Thr Ala
130                 135                 140

Val Glu Asp Asp His Val Val Asp Gly Asn His Met Leu Ala Gly
145                 150                 155                 160

Gln Asn Leu Lys Phe Asn Val Glu Val Val Ala Ile Arg Glu Ala Thr
                165                 170                 175

Glu Glu Glu Leu Ala His Gly His Val His Gly Ala His Asp His His
            180                 185                 190

His Asp His Asp His Asp Gly Cys Cys Gly Gly His
            195                 200
```

<210> SEQ ID NO 11
<211> LENGTH: 149
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: Calmodulin

<400> SEQUENCE: 11

```
Met Ala Asp Gln Leu Thr Cys Cys Glu Gln Cys Cys Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
    50                  55                  60

Tyr Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145
```

<210> SEQ ID NO 12

```
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB0 recombination site

<400> SEQUENCE: 12
agcctgcttt tttatactaa cttgagc                                             27

<210> SEQ ID NO 13
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttP0 recombination site

<400> SEQUENCE: 13
gttcagcttt tttatactaa gttggca                                             27

<210> SEQ ID NO 14
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttL0 recombination site

<400> SEQUENCE: 14
agcctgcttt tttatactaa gttggca                                             27

<210> SEQ ID NO 15
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttR0 recombination site

<400> SEQUENCE: 15
gttcagcttt tttatactaa cttgagc                                             27

<210> SEQ ID NO 16
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB1 recombination site

<400> SEQUENCE: 16
agcctgcttt tttgtacaaa cttgt                                               25

<210> SEQ ID NO 17
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttP1 recombination site

<400> SEQUENCE: 17
```

```
gttcagctttt tttgtacaaa gttggca                                              27
```

<210> SEQ ID NO 18
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttL1 recombination site

<400> SEQUENCE: 18

```
agcctgctttt tttgtacaaa gttggca                                              27
```

<210> SEQ ID NO 19
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttR1 recombination site

<400> SEQUENCE: 19

```
gttcagctttt tttgtacaaa cttgt                                                25
```

<210> SEQ ID NO 20
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB2 recombination site

<400> SEQUENCE: 20

```
acccagctttt cttgtacaaa gtggt                                                25
```

<210> SEQ ID NO 21
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttP2 recombination site

<400> SEQUENCE: 21

```
gttcagctttt cttgtacaaa gttggca                                              27
```

<210> SEQ ID NO 22
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttL2 recombination site

<400> SEQUENCE: 22

```
acccagctttt cttgtacaaa gttggca                                              27
```

<210> SEQ ID NO 23
<211> LENGTH: 25
<212> TYPE: DNA
<213> ORGANISM: Artificial Sequence
<220> FEATURE:
<223> OTHER INFORMATION: Chemically Synthesized
<220> FEATURE:

<223> OTHER INFORMATION: AttR2 recombination site

<400> SEQUENCE: 23
gttcagcttt cttgtacaaa gtggt                                                25

<210> SEQ ID NO 24
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB5 recombination site

<400> SEQUENCE: 24
caactttatt atacaaagtt gt                                                   22

<210> SEQ ID NO 25
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttP5 recombination site

<400> SEQUENCE: 25
gttcaacttt attatacaaa gttggca                                              27

<210> SEQ ID NO 26
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttL5 recombination site

<400> SEQUENCE: 26
caactttatt atacaaagtt ggca                                                 24

<210> SEQ ID NO 27
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttR5 recombination site

<400> SEQUENCE: 27
gttcaacttt attatacaaa gttgt                                                25

<210> SEQ ID NO 28
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB11 recombination site

<400> SEQUENCE: 28
caacttttct atacaaagtt gt                                                   22

<210> SEQ ID NO 29
<211> LENGTH: 27
<212> TYPE: DNA

```
<213> ORGANISM: Artificial Sequence
<220> FEATURE:
<223> OTHER INFORMATION: Chemically Synthesized
<220> FEATURE:
<223> OTHER INFORMATION: AttP11 recombination site

<400> SEQUENCE: 29
gttcaacttt tctatacaaa gttggca                                            27

<210> SEQ ID NO 30
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttL11 recombination site

<400> SEQUENCE: 30
caactttcct atacaaagtt ggca                                               24

<210> SEQ ID NO 31
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttR11 recombination site

<400> SEQUENCE: 31
gttcaacttt tctatacaaa gttgt                                              25

<210> SEQ ID NO 32
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB17 recombination site

<400> SEQUENCE: 32 caactttttgt atacaaagtt gt                                                22

<210> SEQ ID NO 33
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttP17 recombination site

<400> SEQUENCE: 33
gttcaacttt tgtatacaaa gttggca                                            27

<210> SEQ ID NO 34
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttL17 recombination site

<400> SEQUENCE: 34 caactttttgt atacaaagtt ggca                                              24
```

```
<210> SEQ ID NO 35
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttR17 recombination site

<400> SEQUENCE: 35
gttcaacttt tgtatacaaa gttgt                                          25

<210> SEQ ID NO 36
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB19 recombination site

<400> SEQUENCE: 36 caacttttte gtacaaagtt gt                                             22

<210> SEQ ID NO 37
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttP19 recombination site

<400> SEQUENCE: 37
gttcaacttt ttcgtacaaa gttggca                                        27

<210> SEQ ID NO 38
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttL19 recombination site

<400> SEQUENCE: 38 caacttttte gtacaaagtt ggca                                           24

<210> SEQ ID NO 39
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttR19 recombination site

<400> SEQUENCE: 39
gttcaacttt ttcgtacaaa gttgt                                          25

<210> SEQ ID NO 40
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB20 recombination site
```

```
<400> SEQUENCE: 40
caactttttg gtacaaagtt gt                                        22

<210> SEQ ID NO 41
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttP20 recombination site

<400> SEQUENCE: 41
gttcaacttt ttggtacaaa gttggca                                   27

<210> SEQ ID NO 42
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttL20 recombination site

<400> SEQUENCE: 42
caactttttg gtacaaagtt ggca                                      24

<210> SEQ ID NO 43
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttR20 recombination site

<400> SEQUENCE: 43
gttcaacttt ttggtacaaa gttgt                                     25

<210> SEQ ID NO 44
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttB21 recombination site

<400> SEQUENCE: 44
caacttttta atacaaagtt gt                                        22

<210> SEQ ID NO 45
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttP21 recombination site

<400> SEQUENCE: 45
gttcaacttt ttaatacaaa gttggca                                   27

<210> SEQ ID NO 46
<211> LENGTH: 24
<212> TYPE: DNA
<213> ORGANISM: Artificial Sequence
<220> FEATURE:
```

<223> OTHER INFORMATION: Chemically Synthesized
<220> FEATURE:
<223> OTHER INFORMATION: AttL21 recombination site

<400> SEQUENCE: 46 caactttttta atacaaagtt ggca                                   24

<210> SEQ ID NO 47
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: AttR21 recombination site

<400> SEQUENCE: 47 gttcaactttt ttaatacaaa gttgt                                  25

<210> SEQ ID NO 48
<211> LENGTH: 32
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: Encoded attL2

<400> SEQUENCE: 48

Pro Ala Phe Leu Tyr Lys Val Gly Ile Ile Arg Lys His Cys Leu Ser
1               5                   10                  15

Ile Cys Cys Asn Glu Gln Val Thr Ile Ser Gln Asn Lys Ile Ile Ile
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: Encoded by recombination site

<400> SEQUENCE: 49

Pro Ala Phe Leu Tyr Lys Val Gly Ile Ile Arg Lys His Cys Leu Ser
1               5                   10                  15

Ile Cys Cys Asn Glu Gln Val Thr Ile Ser Gln Asn Lys Ile Ile Ile
            20                  25                  30

<210> SEQ ID NO 50
<211> LENGTH: 13
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: target sequence

<400> SEQUENCE: 50

Cys Cys Gly Gly Lys Gly Asn Gly Gly Cys Gly Cys His
1               5                   10

<210> SEQ ID NO 51
<211> LENGTH: 13
<212> TYPE: DNA
<213> ORGANISM: Artificial Sequence
<220> FEATURE:
<223> OTHER INFORMATION: Chemically Synthesized

```
<220> FEATURE:
<223> OTHER INFORMATION: topoisomerase site fusion
<220> FEATURE:
<221> NAME/KEY: misc_feature
<222> LOCATION: (9)..(10)
<223> OTHER INFORMATION: n can be any nucleotide

<400> SEQUENCE: 51
atgcccttnn atg                                                         13

<210> SEQ ID NO 52
<211> LENGTH: 15
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: topoisomerase site with added nucleotides
<220> FEATURE:
<221> NAME/KEY: misc_feature
<222> LOCATION: (9)..(12)
<223> OTHER INFORMATION: n can be any nucleotide

<400> SEQUENCE: 52
atgcccttnn nnatg                                                       15

<210> SEQ ID NO 53
<211> LENGTH: 6
<212> TYPE: PRT
<213> ORGANISM: Artificial Sequence
<220> FEATURE:
<223> OTHER INFORMATION: Chemically Synthesized
<220> FEATURE:
<223> OTHER INFORMATION: tetracysteine

<400> SEQUENCE: 53

Cys Cys Pro Gly Cys Cys
1               5
```